United States Patent
Lee et al.

(10) Patent No.: US 12,077,645 B2
(45) Date of Patent: Sep. 3, 2024

(54) ALGINATE MICROCAPSULES FOR CELL ENCAPSULATION AND, MANUFACTURING METHOD THEREFOR

(71) Applicant: OPTIPHARM CO., LTD, Chungcheongbuk-do (KR)

(72) Inventors: Dong Yun Lee, Seoul (KR); Jae Bin Lee, Incheon (KR); Ki Myung Choi, Sejong-si (KR); Joo Hyun Shim, Chungcheongbuk-do (KR); Jae Kyung Park, Chungcheongbuk-do (KR)

(73) Assignee: OPTIPHARM CO., LTD, Chungcheongbuk-do (KR)

( * ) Notice: Subject to any disclaimer, the term of this patent is extended or adjusted under 35 U.S.C. 154(b) by 884 days.

(21) Appl. No.: 17/042,345

(22) PCT Filed: Apr. 2, 2019

(86) PCT No.: PCT/KR2019/003885
§ 371 (c)(1),
(2) Date: Sep. 28, 2020

(87) PCT Pub. No.: WO2019/194543
PCT Pub. Date: Oct. 10, 2019

(65) Prior Publication Data
US 2021/0017348 A1   Jan. 21, 2021

(30) Foreign Application Priority Data
Apr. 2, 2018 (KR) .................. 10-2018-0038205

(51) Int. Cl.
C08J 7/04 (2020.01)
A61K 9/50 (2006.01)
A61K 31/353 (2006.01)
A61K 35/39 (2015.01)

(52) U.S. Cl.
CPC .................... *C08J 7/04* (2013.01); *A61K 9/50* (2013.01); *A61K 31/353* (2013.01); *A61K 35/39* (2013.01); *C08J 2305/04* (2013.01)

(58) Field of Classification Search
CPC ............ A61K 47/55; A61K 9/50; B01J 15/22
See application file for complete search history.

(56) References Cited

FOREIGN PATENT DOCUMENTS

| CN | 106470666 A | * 3/2017 | ............ A61K 38/39 |
|---|---|---|---|
| JP | 2002514253 A | * 5/2002 | |
| JP | 2016519079 A | 6/2016 | |
| KR | 20160041166 A | 4/2016 | |
| WO | 0053159 | 9/2000 | |
| WO | WO-2010138082 A1 | * 12/2010 | ........... A61K 31/015 |

OTHER PUBLICATIONS

Paques, Jerome P., et al. "Preparation Methods of Alginate Nanoparticles," Advances in Colloid and Interface Science, vol. 209, pp. 163-171(2014).
Shutava, Tatsiana G., et al. "Layer-by-Layer-Coated Gelatin Nanoparticles as a Vehicle for Delivery of Natural Polyphenols," ACS Nano, V. 3.7, pp. 1877-1885 (2009).
Desai, Tejal, and Lonnie D. Shea. "Advances in islet encapsulation technologies." Nature reviews Drug discovery 16.5 (2017): 338-350.

* cited by examiner

Primary Examiner — Kyle A Purdy
(74) Attorney, Agent, or Firm — Hoffmann & Baron, LLP

(57) ABSTRACT

The present disclosure provides a surface-modified alginate micro-capsule having a core-shell structure in which a core is fluidizable phase alginate, and a shell is alginate hydrogel crosslinked with epigallocatechin gallate dimer, a preparation method thereof, and a cell encapsulation method using the same.

5 Claims, 22 Drawing Sheets

ALGINATE MICROCAPSULES FOR CELL ENCAPSULATION AND, MANUFACTURING METHOD THEREFOR

CROSS-REFERENCE TO RELATED APPLICATIONS

This application is a National Phase application of International Application No. PCT/KR2019/003885 filed Apr. 2, 2019 which claims priority to the Korean Patent Application No. 10-2018-0038205 filed Apr. 2, 2018, the disclosures of which are incorporated herein by reference.

TECHNICAL FIELD

The present disclosure relates to a surface-modified alginate micro-capsule, a preparation method thereof, and a cell encapsulation method using the same. More specifically, the present disclosure relates to a surface-modified alginate micro-capsule which may be used for cell encapsulation to protect cells from external environments in cell transplantation, and may improve cell viability, a preparation method thereof, and a cell encapsulation method using the same.

BACKGROUND

Because alginate is excellent in biocompatibility and is bio-inactive, it is used as a biomaterial in various fields such as tissue engineering, cell therapy, and artificial organ fabrication.

In the treatment of type 1 diabetes, islet cell transplantation has been suggested as an effective treatment scheme. However, because allogeneic transplantation is highly demanded but poorly supplied, xenogeneic transplantation is required. Because transplanted cells may be destroyed due to the immune response of the transplanted subject in the xenogeneic transplantation, it is important to suppress the immune response. Research on encapsulation using biomaterials to protect xenogeneic cells to be transplanted was conducted. Alginate has been suggested as an encapsulation material to prevent exposure of islet to immune responses in islet cell transplantation for diabetes treatment [Desai et al. Nature reviews Drug discovery 16.5 (2017), 338].

The representative material used for islet encapsulation is alginate hydrogel. The alginate hydrogel may be prepared quickly and easily by crosslinking sodium alginate using a divalent cation such as Ca'. However, in an environment in which a large amount of monovalent cations such as Na is present, the monovalent cation may be exchanged with the divalent cation used for crosslinking, so that the hydrogel may be subjected to a sol-gel phase transition in a solution state. On the other hand, the body is an environment in which a large amount of $Na^+$ exists. Therefore, during transplantation in the body, alginate hydrogel used for encapsulation has a problem of gradually melting in the body because $Ca^{2+}$ is exchanged for $Na^+$ in the body or naturally diffuses. This melting shortens the life of the micro-capsule. This causes the internal cells to fail to be protected from the external immune system. Thus, those become limitations in commercialization of micro-encapsulated islets. In addition, the formed hydrogel prevents the cells from being completely engrafted, thus causing hypoxia and the like in the cells. In addition, there is a limitation in that the diffusion amount of oxygen or nutrients is small compared to the volume of the capsule itself.

In order to overcome these limitations, many studies have recently been conducted on the development of alginate conjugates that form hydrogels in an independent manner from $Ca^{2+}$, hollow capsules, surface-modified cells, and the like. Alginate-dopamine conjugate and hyaluronic acid-EGCG conjugate were developed as the alginate conjugates that form the hydrogels in the independent manner from $Ca^{2+}$. The alginate-dopamine conjugate may be formed via oxidation of dopamine. However, $H_2O_2$ and HRP enzymes are required for binding between alginate and dopamine, and the binding is not strong, and functionality such as antiproliferative effect and radical scavenging is somewhat inferior. In the hyaluronic acid-EGCG conjugate, the hyaluronic acid is a substance that may be decomposed naturally in the body. Thus, the prepared conjugate may be decomposed in vivo. The hydrogel formation reaction rate via the EGCG binding is low. The physical properties thereof are not strong. Thus, the hyaluronic acid-EGCG conjugate may not be applied to micro-encapsulation.

SUMMARY

The purpose of the present disclosure is to provide a surface-modified alginate micro-capsule for cell encapsulation.

Another purpose of the present disclosure is to provide a preparation method of a surface-modified alginate micro-capsule for cell encapsulation.

Another purpose of the present disclosure is to provide a cell encapsulation method using the surface-modified alginate micro-capsule.

In order to achieve the purposes, the present disclosure provides a surface-modified alginate micro-capsule having a core-shell structure in which a core is fluidizable phase alginate, and a shell is alginate hydrogel crosslinked with epigallocatechin gallate dimer.

According to the present disclosure, some of the epigallocatechin gallate dimers of the shell may be coupled to other epigallocatechin gallate dimers via oxidation.

According to the present disclosure, the shell may further include an alginate coating layer.

According to the present disclosure, the alginate coating layer may have an amide bond with the epigallocatechin gallate dimer of the shell.

According to the present disclosure, the shell may contain a plurality of hollows connected to each other in three dimensions.

According to the present disclosure, the core may be a liquid phase alginate or a mixture of liquid phase alginate and alginate hydrogel.

According to the present disclosure, the micro-capsule may be intended for cell encapsulation. Preferably, the micro-capsule may be intended for islet cell encapsulation.

Further, the present disclosure provides a method for preparing a surface-modified alginate micro-capsule, the method including (1) a core preparation step of preparing a calcium-alginate micro-capsule; (2) a shell preparation step in which an alginate-epigallocatechin gallate dimer crosslinked product is formed on a surface of the calcium-alginate micro-capsule by reacting the calcium-alginate micro-capsule and the epigallocatechin gallate dimer with each other; and (3) a core liquefaction step of chelating calcium ions of calcium-alginate to an epigallocatechin gallate dimer, in which the core is the fluidizable phase alginate, and the shell is alginate hydrogel crosslinked with epigallocatechin gallate dimer.

According to the present disclosure, the method may further include a step of bonding the epigallocatechin gallate dimer of the prepared shell with adjacent epigallocatechin gallate dimer thereto via oxidation.

In accordance with the present disclosure, the method may further include coating the prepared shell with alginate.

According to the present disclosure, the method may further include a step of forming a hollow by reacting the prepared surface-modified alginate micro-capsule with a calcium ion chelating agent.

Further, the present disclosure provides a cell encapsulation method using a surface-modified alginate micro-capsule having a core-shell structure, the method including (a) a core preparation step of encapsulating cells with calcium-alginate hydrogel micro-capsules; (b) a shell preparation step of reacting the calcium-alginate hydrogel micro-capsule encapsulating the cells with an epigallocatechin gallate dimer to form an alginate-epigallocatechin gallate dimer crosslinked product on a surface of the calcium-alginate micro-capsule; and (c) a step of chelation of calcium ions of the calcium-alginate to the epigallocatechin gallate dimer to liquefy the hydrogel around the cell.

According to the present disclosure, the method may further include a step of bonding the epigallocatechin gallate dimer of the prepared shell with an adjacent epigallocatechin gallate dimer thereto via oxidation.

In accordance with the present disclosure, the method may further include coating the prepared shell with alginate.

According to the present disclosure, the method may further include a step of forming a hollow by reacting the prepared surface-modified alginate micro-capsule with a calcium ion chelating agent.

According to the present disclosure, the cells may be cells for transplantation in vivo. Preferably, the cell may be an islet cell.

In the alginate micro-capsule according to the present disclosure, the alginate may be cross-linked to EGCG via oxidation of EGCG. Thus, the hydrogel may be formed in an independent manner from $Ca^{2+}$. In addition, in the alginate micro-capsule according to the present disclosure, the hydrogel may not be easily decomposed in vivo because EGCG chelates $Ca^{2+}$ of the alginate hydrogel thereto. Further, because the inner alginate core is partially dissolved, oxygen or nutrients are diffused and easily delivered to the inner encapsulated cells, thereby improving cell viability and excellent physical properties. Further, the hydrogel may not be easily decomposed in vivo. Therefore, the ability to protect the internal cells from external physical stimuli may be improved, and the immune response may be minimized.

Figure 22:
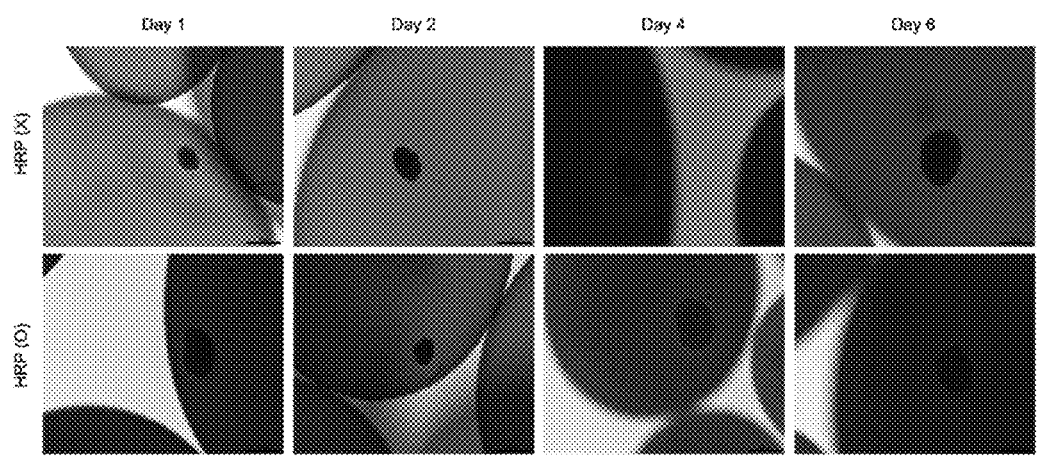

A top of FIG. 22 shows the optical microscope image of islets encapsulated surface-modified alginate micro-capsule without HRP and a bottom of FIG. 22 shows the optical microscope image of islets encapsulated surface-modified alginate micro-capsule having HRP added.

Figure 23:
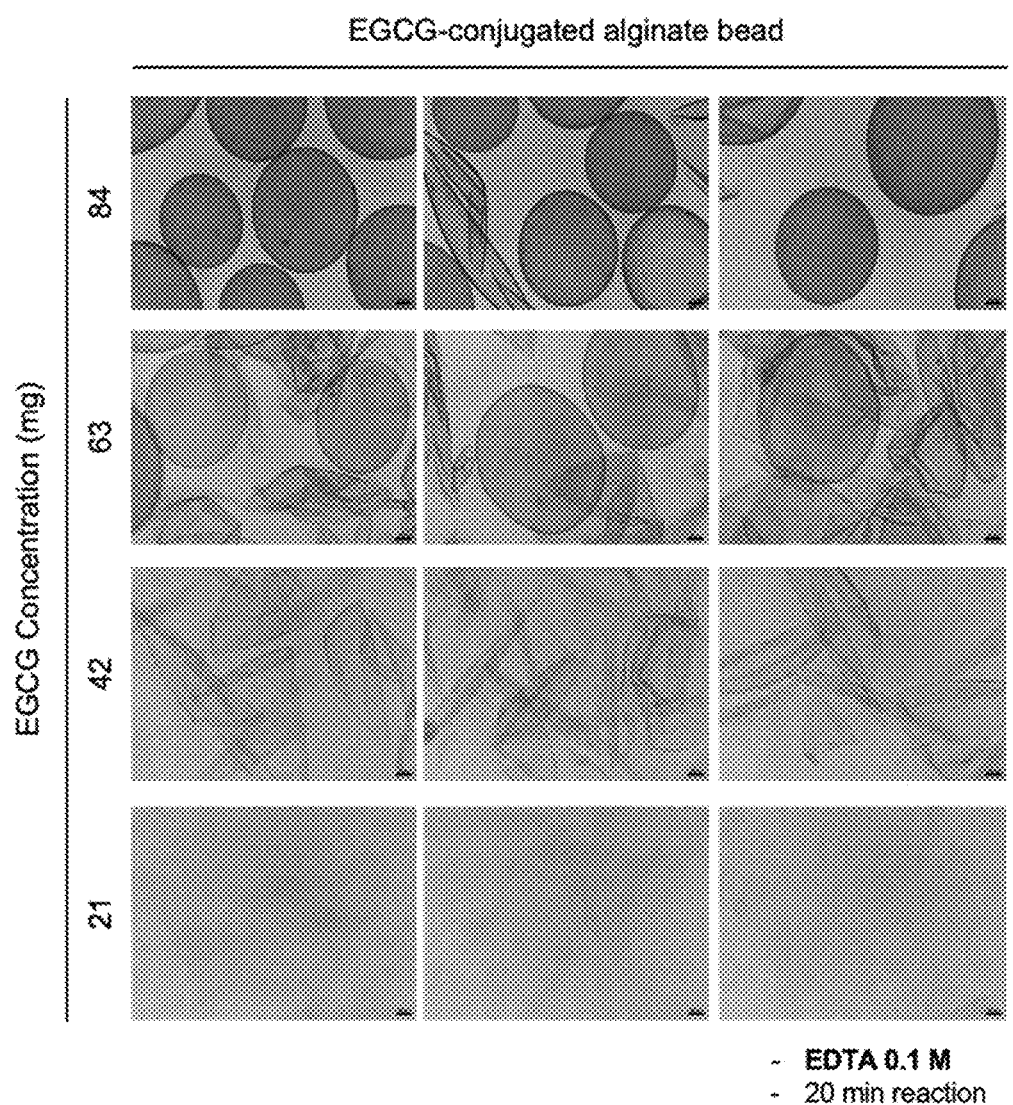

FIG. 23 shows the decomposition resistance of the surface-modified micro-capsule based on the EGCG content as concentration using an optical microscope image.

Figure 24:
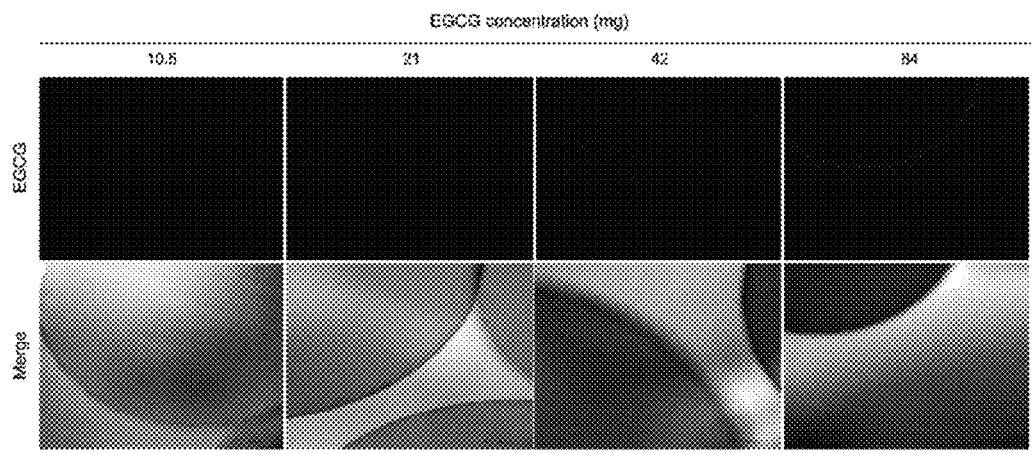

FIG. 24 shows the identification of whether an outer EGCG layer of the surface-modified micro-capsule is formed based on the EGCG content using an optical microscope.

Figure 25:
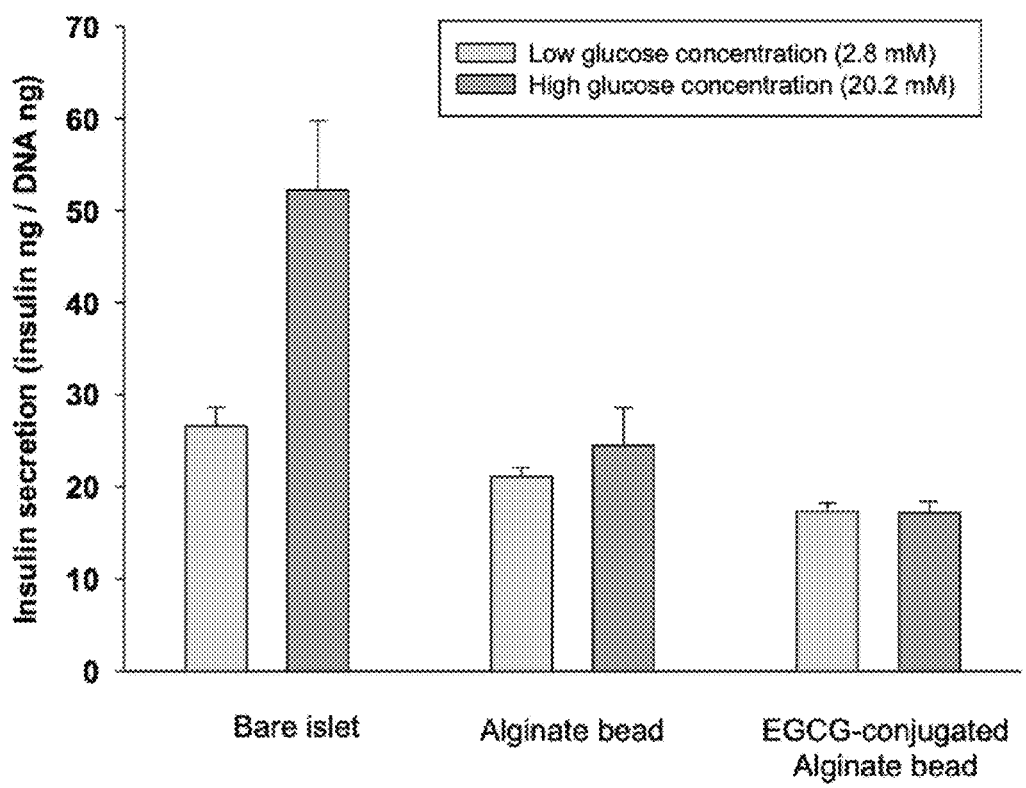

FIG. 25 is a graph showing the insulin secretion ability of the islet inside the micro-capsule.

Figure 26:
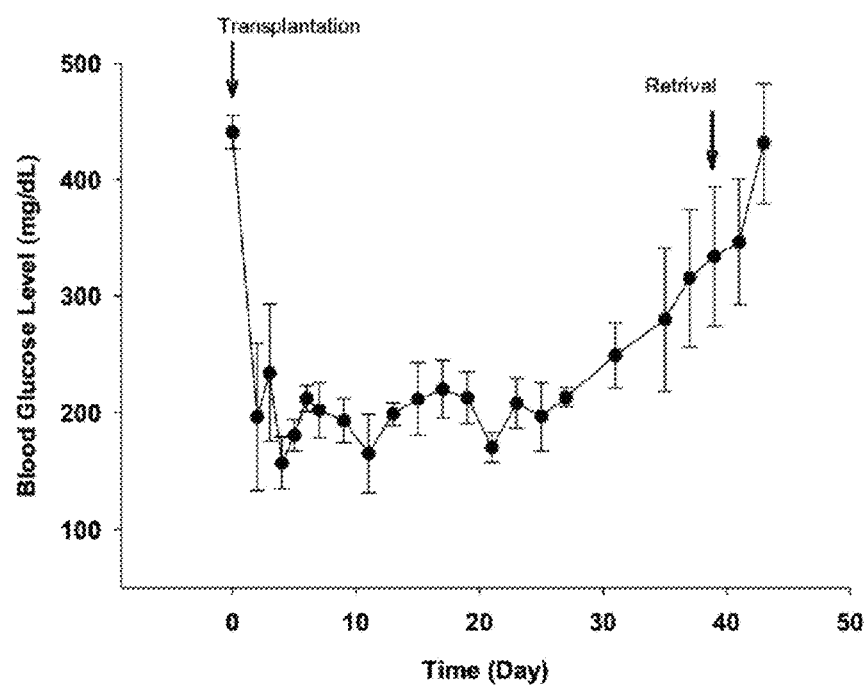
Figure 26:
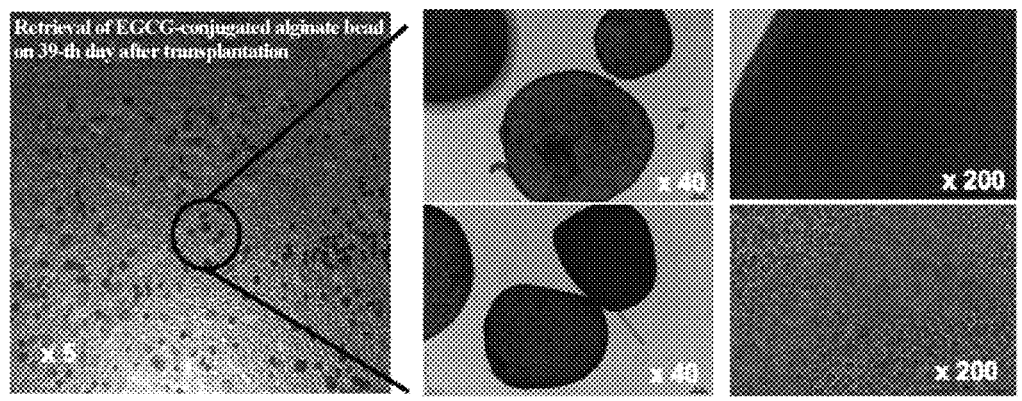

FIG. 26 is a graph showing the in-blood glucose concentration of islet in the surface-modified micro-capsule when 84 mg of EGCG is used.

Figure 27:
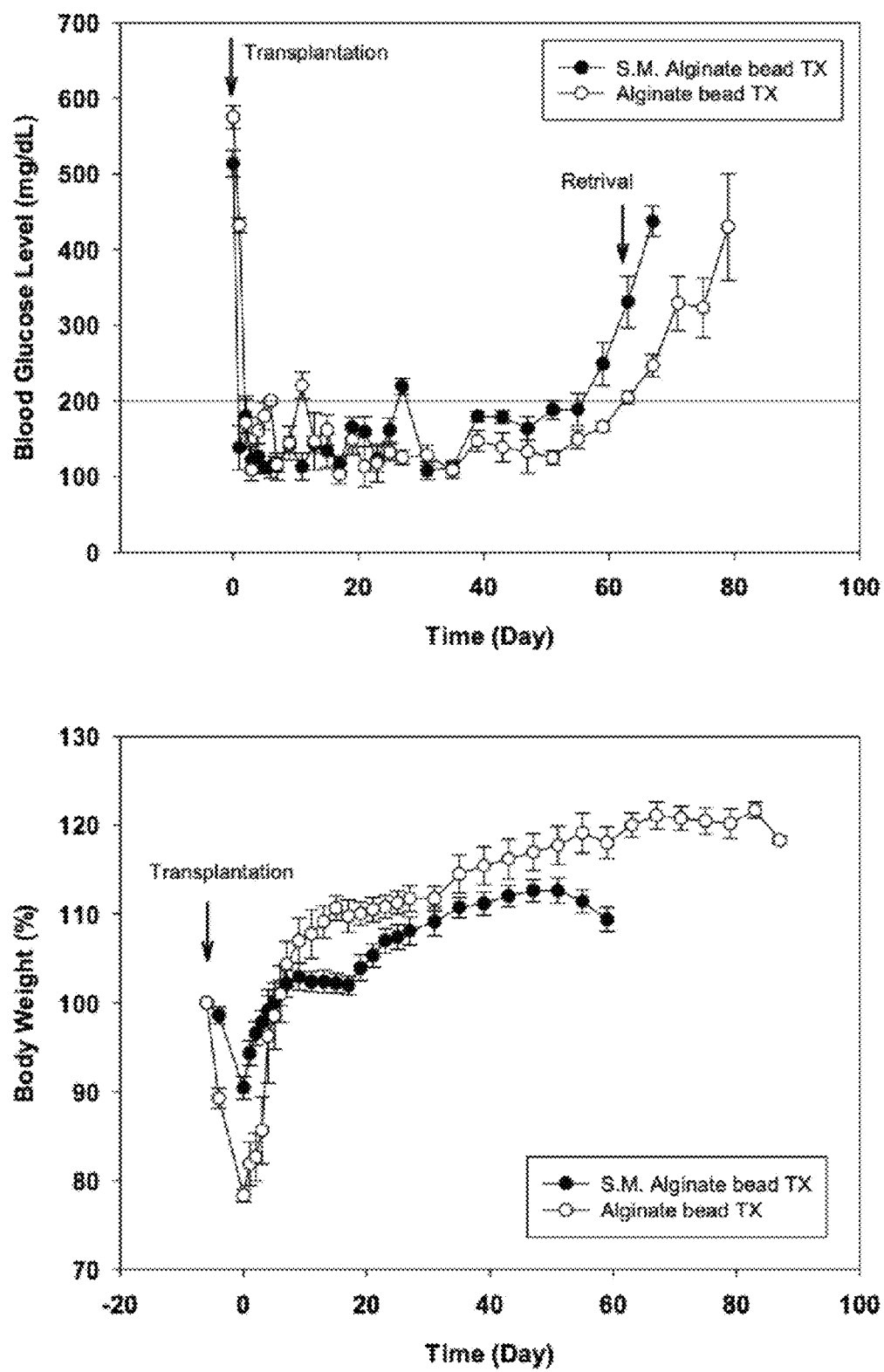

FIG. 27 is a graph showing the in-blood glucose concentration and weight of each of alginate micro-capsule and surface-modified alginate micro-capsule.

Figure 28:
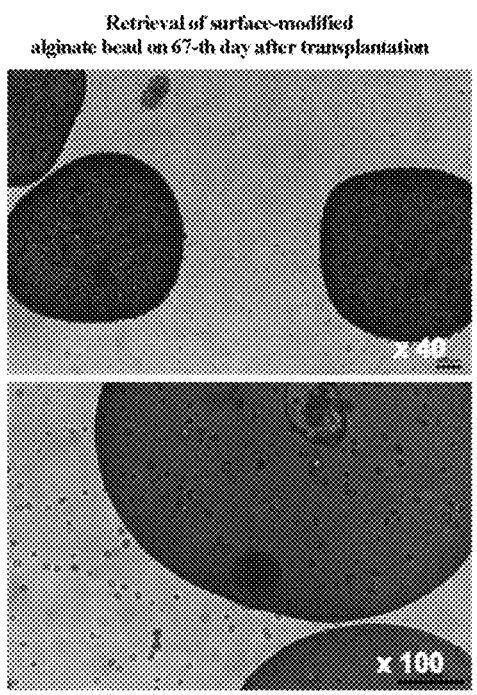
Figure 28:
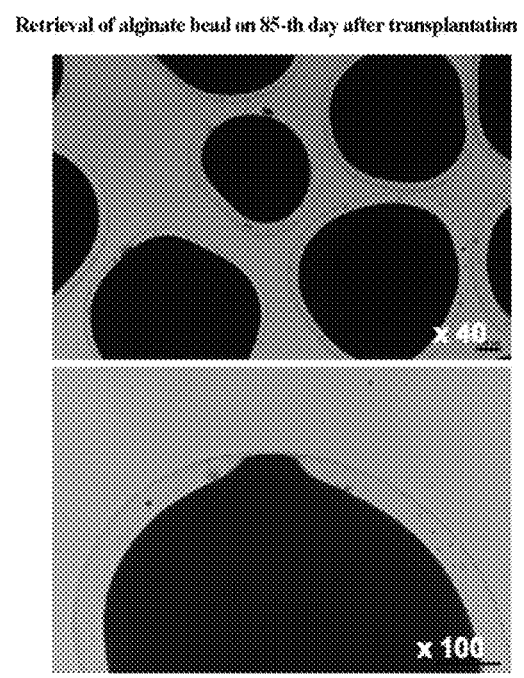

FIG. 28 shows a shape of each of the surface-modified micro-encapsulated islet and the alginate micro-encapsulated islet using an optical microscope.

DETAILED DESCRIPTION

Hereinafter, the present disclosure will be described in more detail.

The present disclosure provides a surface-modified alginate micro-capsule having a core-shell structure in which a core is fluidizable phase alginate, and a shell is alginate hydrogel crosslinked with epigallocatechin gallate dimer.

According to the present disclosure, the core may have a fluidizable phase. The fluidizable phase may be a liquid phase or a mixture of liquid phase and hydrogel. When the core has a fluidizable phase, oxygen and substances may be easily delivered to the cells therein, thereby to improve cell viability.

According to the present disclosure, the epigallocatechin gallate dimer may be formed via the reaction of #6 and #8 carbons of the epigallocatechin monomer with aldehyde. The epigallocatechin gallate dimer may be at least one selected from an 8-8 isomer, 6-8 isomers (2 types) and a 6-6 isomer, and preferably a mixture of these 4 types.

The epigallocatechin gallate 8-8 dimer is as defined in a following Formula 1.

[Formula 1]

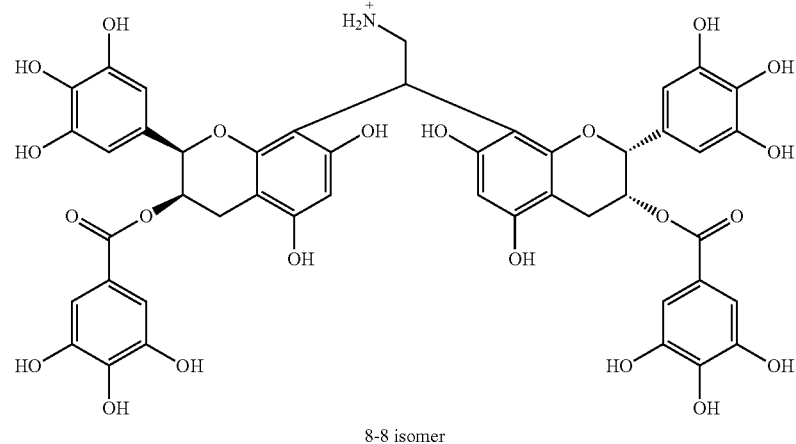

8-8 isomer

A pair of epigallocatechin gallate 6-8 dimers are as defined in the following Formulas 2 and 3.

[Formula 2]

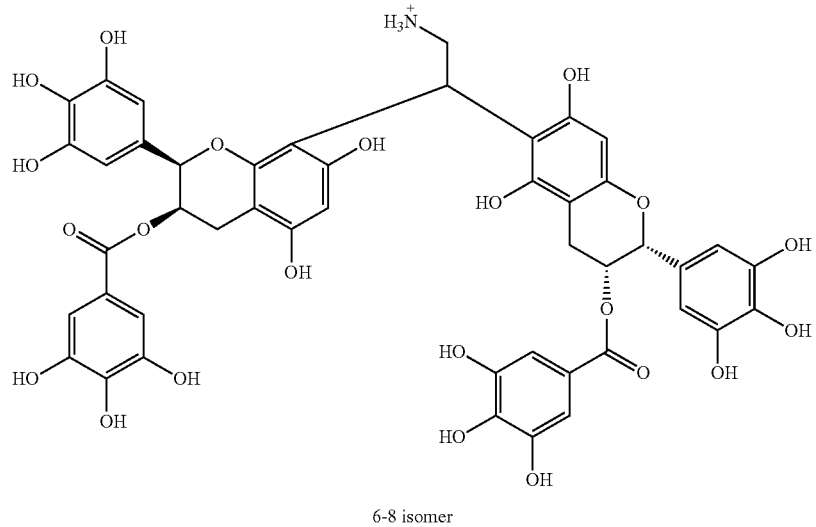

6-8 isomer

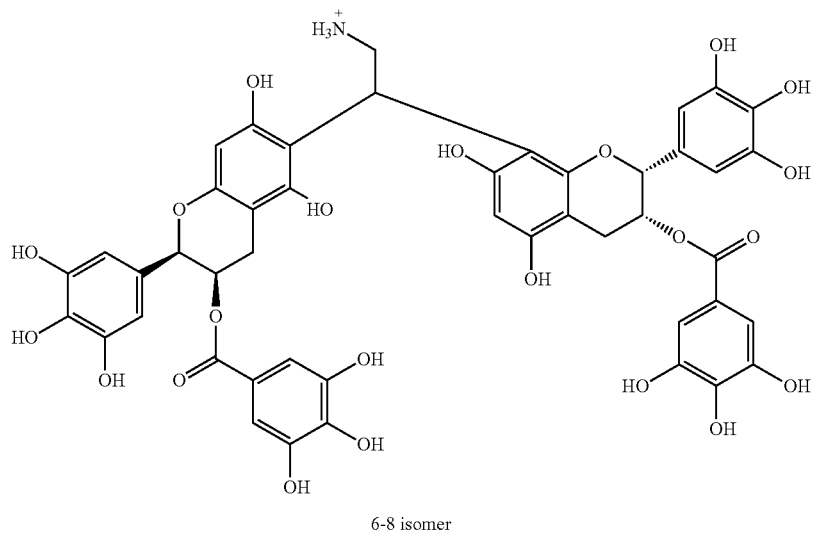

6-8 isomer

The epigallocatechin gallate 6-6 dimer is as defined in the following Formula 4.

[Formula 4]

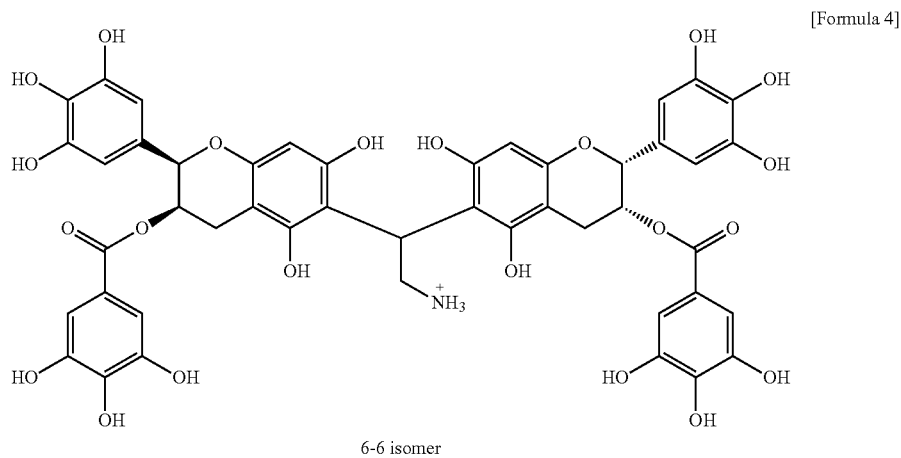 [SMILES: NCC(c1c(O)cc2c(c1O)C[C@@H](OC(=O)c1cc(O)c(O)c(O)c1)[C@@H](c1cc(O)c(O)c(O)c1)O2)c1c(O)cc2c(c1O)C[C@@H](OC(=O)c1cc(O)c(O)c(O)c1)[C@@H](c1cc(O)c(O)c(O)c1)O2]

6-6 isomer

According to the present disclosure, some of the epigallocatechin gallate dimers of the shell may be coupled to other epigallocatechin gallate dimers via oxidation. The oxidation-based bonding between the epigallocatechin gallate dimers may thicken the shell. The oxidation-based bonding between the epigallocatechin gallate dimers may improve the physical properties of the micro-capsule according to the present disclosure and thus may be effective in protecting the encapsulated cells from physical shock. The oxidatively bonded epigallocatechin gallate dimers are shown in the following Formula 5.

[Formula 5]
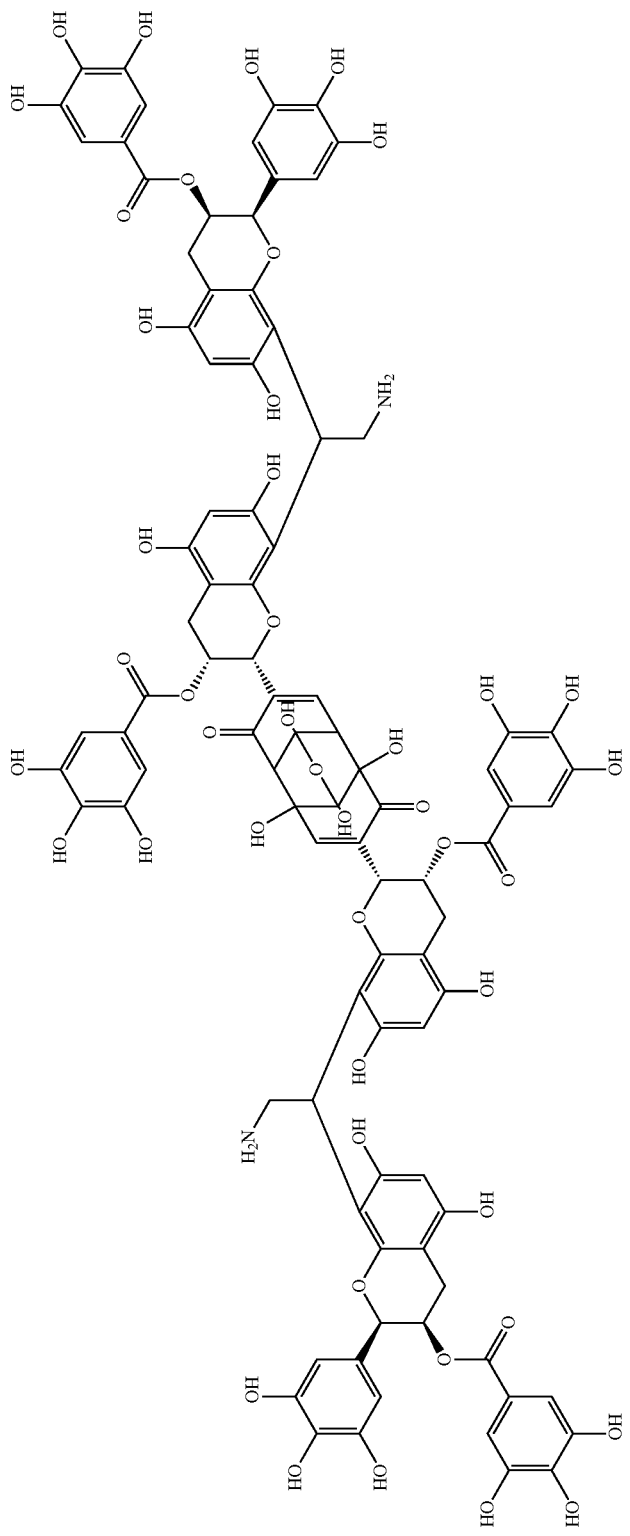

According to the present disclosure, the shell may further include an alginate coating layer.

According to the present disclosure, the alginate coating layer may have an amide bond with the epigallocatechin gallate dimer of the shell.

As shown in the Formula 5, epigallocatechin gallate dimer contains an amine group and thus exhibits positive charge. According to conventional studies, positively charged biomaterials may induce more immune responses and inflammation than neutral or negatively charged biomaterials may induce. The formation of the alginate coating layer is preferable because the amine group of the epigallocatechin gallate dimer and the —COOH group of the alginate form an amide bond, so that the capsule may not exhibit positive charge.

According to the present disclosure, the shell may contain a plurality of hollows connected to each other in three dimensions. The formation of the hollow is preferable because the oxygen and substances may be easily delivered to the internal cells through the hollow. The hollow may be easily formed by treating a surface-modified alginate micro-capsule having a core-shell structure according to the present disclosure with a calcium ion chelating agent.

According to the present disclosure, the micro-capsule may be intended for cell encapsulation. The type of cell is not limited to a specific type. The cell may be a cell for transplantation in vivo. Preferably, the cell may be an islet cell.

In the present disclosure, the term "islet" means Langerhans islets, and the islet transplantation is a practical treatment for the improvement of type 1 diabetes. In this connection, the islet contains insulin-secreting beta cells. Thus, transplantation of islets may treat insulin-dependent type 1 diabetes.

Further, the present disclosure provides a method for preparing a surface-modified alginate micro-capsule, the method including (1) a core preparation step of preparing a calcium-alginate micro-capsule; (2) a shell preparation step in which an alginate-epigallocatechin gallate dimer crosslinked product is formed on a surface of the calcium-alginate micro-capsule by reacting the calcium-alginate micro-capsule and the epigallocatechin gallate dimer with each other; and (3) a core liquefaction step of chelating calcium ions of calcium-alginate to an epigallocatechin gallate dimer, in which the core is the fluidizable phase alginate, and the shell is alginate hydrogel crosslinked with epigallocatechin gallate dimer.

First, the method may include preparing the calcium-alginate micro-capsule.

Next, the calcium-alginate micro-capsule is reacted with the epigallocatechin gallate dimer. As a result of the reaction, alginate of the calcium-alginate hydrogel is crosslinked with epigallocatechin gallate dimer to form a hydrogel as the shell. Some or all of the calcium ions in the internal calcium-alginate are chelated to the epigallocatechin gallate dimer. When all of the calcium ions are chelated to the epigallocatechin gallate dimer, the inner alginate turns into a liquid phase. When only some of the calcium ions are chelated to the epigallocatechin gallate dimers, liquid phase alginate and calcium-alginate hydrogel coexist as an inner portion to form a fluidizable phase slurry.

The micro-capsule may be an islet cell capsule comprising islet cells.

In the present disclosure, the term "islet cell capsule" means surrounding islet cells with a biocompatible polymer to form a capsule shape. This islet cell capsule prevents the penetration of immune cells, thereby suppressing immune rejection caused by islets isolated from xenogenic subjects or islets isolated from allogeneic subjects.

According to the present disclosure, the method may further include a step of bonding the epigallocatechin gallate dimer of the prepared shell with an adjacent epigallocatechin gallate dimer thereto via oxidation. The oxidation scheme is not particularly limited as long as it is commonly used for the oxidation of epigallocatechin gallate dimer. However, use of HRP (horseradish peroxidase) enzyme involved in the catalytic reaction of dehydrogenating the substrate is more preferable.

In accordance with the present disclosure, the method may further include coating the prepared shell with alginate. The coating may be carried out via reaction by adding a pure alginate solution thereto.

According to the present disclosure, the method may further include a step of forming a hollow by reacting the prepared surface-modified alginate micro-capsule with a calcium ion chelating agent. The calcium ion chelating agent may be EDTA, in one example.

Further, the present disclosure provides a cell encapsulation method using a surface-modified alginate micro-capsule having a core-shell structure, the method including (a) a core preparation step of encapsulating cells with calcium-alginate hydrogel micro-capsules; (b) a shell preparation step of reacting the calcium-alginate hydrogel micro-capsule encapsulating the cells with an epigallocatechin gallate dimer to form an alginate-epigallocatechin gallate dimer crosslinked product on a surface of the calcium-alginate micro-capsule; and (c) a step of chelation of calcium ions of the calcium-alginate to the epigallocatechin gallate dimer to liquefy the hydrogel around the cell.

According to the present disclosure, the method may further include a step of bonding the epigallocatechin gallate dimer of the prepared shell with an adjacent epigallocatechin gallate dimer thereto via oxidation.

In accordance with the present disclosure, the method may further include coating the prepared shell with alginate.

According to the present disclosure, the method may further include a step of forming a hollow by reacting the prepared surface-modified alginate micro-capsule with a calcium ion chelating agent.

According to the present disclosure, the cells may be cells for transplantation in vivo. Preferably, the cell may be an islet cell.

According to the present disclosure, the concentration of the epigallocatechin gallate used in the micro-capsule preparation may preferably be in a range of 42 mg to 167 mg per 5 mg of alginate, and more preferably, may be 63 to 167 mg per 5 mg of alginate, and still more preferably, may be 84 to 167 mg per 5 mg of alginate. In one of the most desirable implementations according to the present disclosure, the concentration of epigallocatechin gallate per 5 mg of alginate is 84 mg.

In an aspect according to the present disclosure, the present disclosure provides a composition for treatment of diabetes, the composition containing the islet cell capsule for use in preventing or treating diabetes.

The diabetes treatment may preferably be carried out via transplantation of the capsule into a living body. The present inventors have identified that the islet cell capsule according to the present disclosure has high viability, has a high ability to secrete insulin in response to glucose, metabolites are permeable therethrough, but immune cells are not permeable therethrough. Thus, the present inventors have identified that the diabetes may be treated via transplantation of the islet cell capsule according to the present disclosure into a small area of the body to secrete insulin without administration of an immunosuppressant.

In the present disclosure, the term "treatment" refers to any action in which diabetes symptoms are ameliorated or beneficially altered by administering the composition containing the islet cell capsules according to the present disclosure. The diabetes treatment may be applied to any mammal that may have developed diabetes. Examples thereof include not only humans and primates, but also livestock such as cattle, pigs, sheep, horses, dogs and cats, but preferably humans.

The islet cell capsule according to the present disclosure may be transplanted to patients in need of diabetes treatment. The transplantation site is preferably abdominal cavity, subcutaneous, intramuscular, internal organs, organ arterial/venous vascular, brain-spinal fluid or lymph fluid. Further, the islet cell capsule according to the present disclosure may be administered to a patient in need of diabetes treatment without administration of an immunosuppressant, but preferably combination with an immunosuppressant or an anti-inflammatory agent. The immunosuppressant may be, but is not limited to, selected from the group consisting of cyclosporine, sirolimus, rapamycin and ortacrolimus.

The anti-inflammatory agent may be, but is not limited to, selected from the group consisting of aspirin, ibuprofen, steroidal and non-steroidal anti-inflammatory agents. The immunosuppressant or anti-inflammatory agent is preferably administered for 6 months after the transplantation of the islet capsule, preferably for 1 month after the transplantation of the islet capsule.

The composition may further include a pharmaceutically acceptable carrier and may be formulated with a carrier. In the present disclosure, the term "pharmaceutically acceptable carrier" refers to a carrier or diluent that does not irritate an organism and does not impair the biological activity and properties of the administered capsule. The pharmaceutically acceptable carriers for the composition formulated as a liquid solution may have sterilization and may be biocompatible, and thus may include saline, sterile water, Ringer's solution, buffered saline, albumin injection solution, dextrose solution, maltodextrin solution, glycerol, ethanol, and a mixture of one or more of these ingredients. When necessary, other conventional additives such as antioxidants, buffers, and bacteriostatic agents may be added thereto. Further, when additionally adding a diluent, a dispersant, a surfactant, a binder, and a lubricant thereto, the composition may be formulated into a formulation for injection such as an aqueous solution, suspension, or emulsion.

For transplantation of the islet cell capsules according to the present disclosure to recipients, the amount of islet capsules as transplanted may be preferably 4,000 to 10,000 IEQ/kg for a mouse, and may be 10,000 to 15,000 IEQ/kg for non-human primate and may vary depending on the type of donor, sex and pancreatic condition of the donor, the recipient's weight, age, sex, health status, diet, administration time, administration method, excretion rate, and disease severity.

In another aspect, the present disclosure provides a method of treating diabetes, the method including administering the composition to a subject suffering from diabetes or a subject at risk of having developed diabetes.

The term "administration" as used in the present disclosure means introducing a given substance to the patient in any suitable way. The route of administration of the composition may be administered through any general route as long as the composition may reach the target tissue. The route may include intraperitoneal administration, intravenous administration, intramuscular administration, subcutaneous administration, intradermal administration, oral administration, topical administration, intranasal administration, intrapulmonary administration, and rectal administration, but is not limited thereto. Further, the composition may be administered using any device capable of moving to the target site.

In another aspect, the present disclosure provides the use of the composition containing the micro-capsule to produce a drug for preventing or treating diabetes. Hereinafter, the present disclosure will be described in more detail with reference to preferred Examples. However, these Examples are intended to explain the present disclosure in more detail. It will be apparent to those of ordinary skill in the art that the scope of the present disclosure is not limited thereto.

EXAMPLES

Synthesis Example 1. Preparation of Epigallocatechin Gallate (EGCG) Dimer 2,2-diethoxyethylamine (DA) exists as an aldehyde in an acidic environment. EGCG dimer was prepared by reacting epigallocatechin gallate (EGCG) and DA in methanesulfonic acid (MSA) to allow aldehyde mediated polymerization.

Specifically, 3.8 ml of tetrahydrofuran and 7 μl of methanesulfonic acid were mixed in a 10 ml vial, then 2.29 g (5 mmol) of EGCG was added under dark condition and nitrogen atmosphere, followed by stirring for 1 to 2 hours. Next, Then, 145 μl of 2,2-diethoxyethylamine was added to a mixed solvent of 1 ml of tetrahydrofuran and 0.2 ml of methanesulfonic acid in a cooled-down 10 ml vial, followed by stirring for 20 to 30 minutes, such that an ethoxy group was removed from 2,2-diethoxyethylamine and aldehyde group was exposed. A solution of 2,2-diethoxyethylamine from which the ethoxy group had been removed was slowly added dropwise to the previously prepared EGCG solution and reacted overnight under dark condition at room temperature. After completion of the reaction, the reaction mixture was transferred to a flask, and the solvent was removed by reducing pressure. Next, the inside of the flask was exchanged for nitrogen atmosphere and then sealed. Under dark condition, 10 ml of deionized water was added to the sealed flask using a syringe, followed by stirring. After completion of the reaction, ethyl acetate and distilled water were added to the reaction mixture under dark condition and then it was separated into organic and water phase using a separatory funnel. The water phase was rapidly frozen and then freeze-dried to obtain the desired EGCG dimer. The prepared EGCG dimer was stored in a cryogenic freezer before use.

Figure 1:
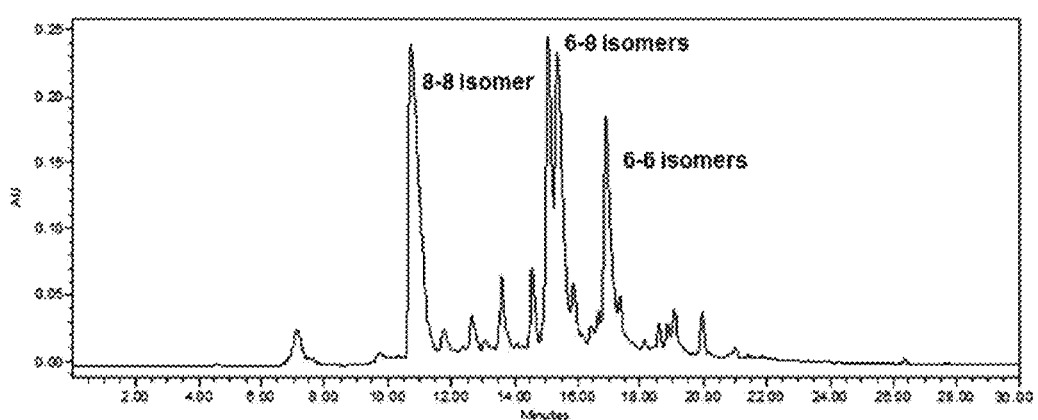
FIG. 1 is the result of analyzing epigallocatechin gallate (EGCG) dimer prepared according to the present disclosure via high performance liquid chromatography.
Figure 2:
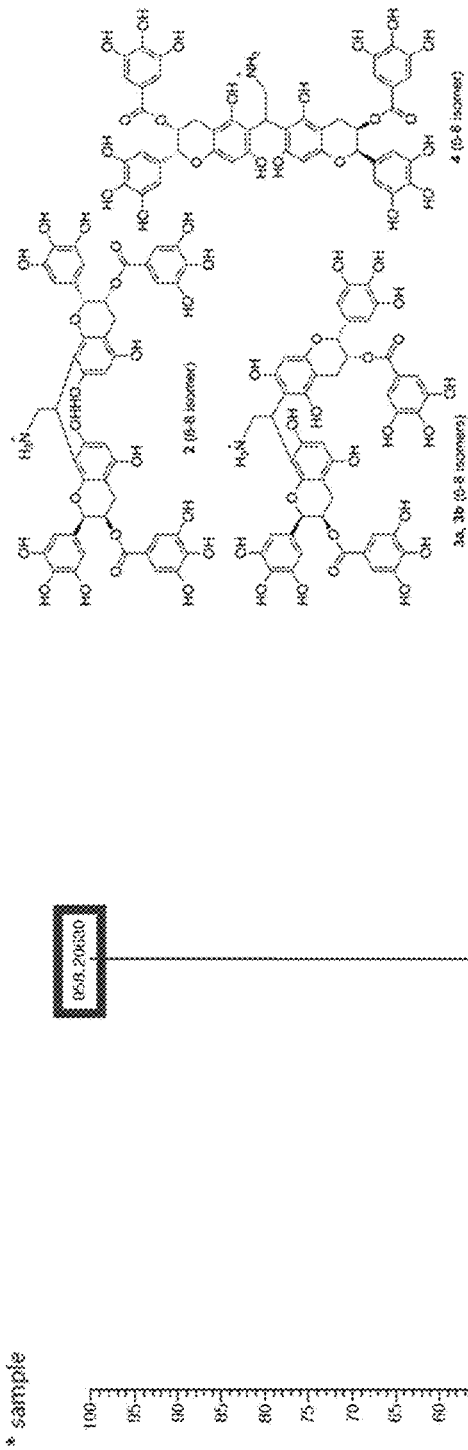
FIG. 2 is the result of analyzing epigallocatechin gallate (EGCG) dimer prepared according to the present disclosure using a mass spectrometer.
Figure 2:
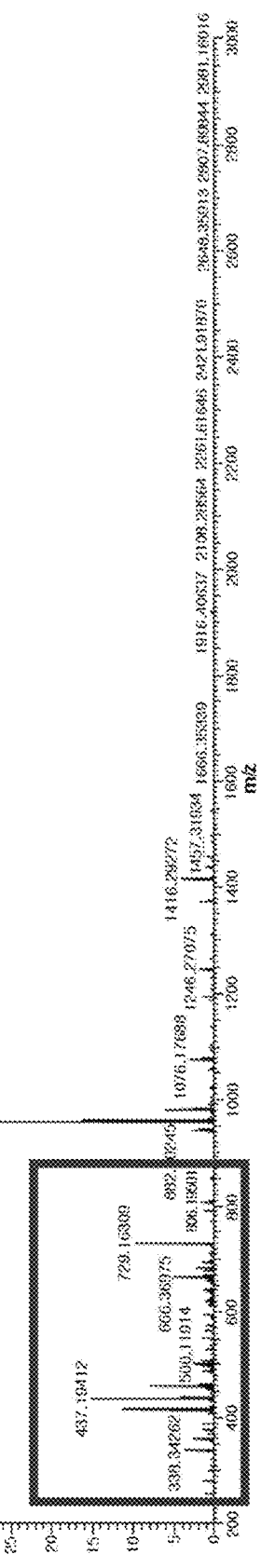

As may be seen in Scheme 1 below, #6 and #8 carbons react with the aldehyde to form a dimer. In this connection, the EGCG dimer as prepared according to the binding type was obtained as a mixture of the 8-8 isomer, 6-8 isomers (2 types) and the 6-6 isomer. To identify this mixture, the prepared EGCG dimer was analyzed using high performance liquid chromatography (HPLC) and mass spectrometry. FIG. 1 is a result of HPLC, and FIG. 2 is a result of the mass spectrometry. As shown in FIG. 1, the synthesis of the 4 types of EGCG dimers was observed. Whereas, when the EGCG dimer was not synthesized normally, and was formed as an aggregates, a peak appeared in the 6 to 6.4-minute range.

HRMS-ESI: $C_{46}H_{40}NO_{22}$ [M+H]+Calculated for 958.2036, observed 958.2062

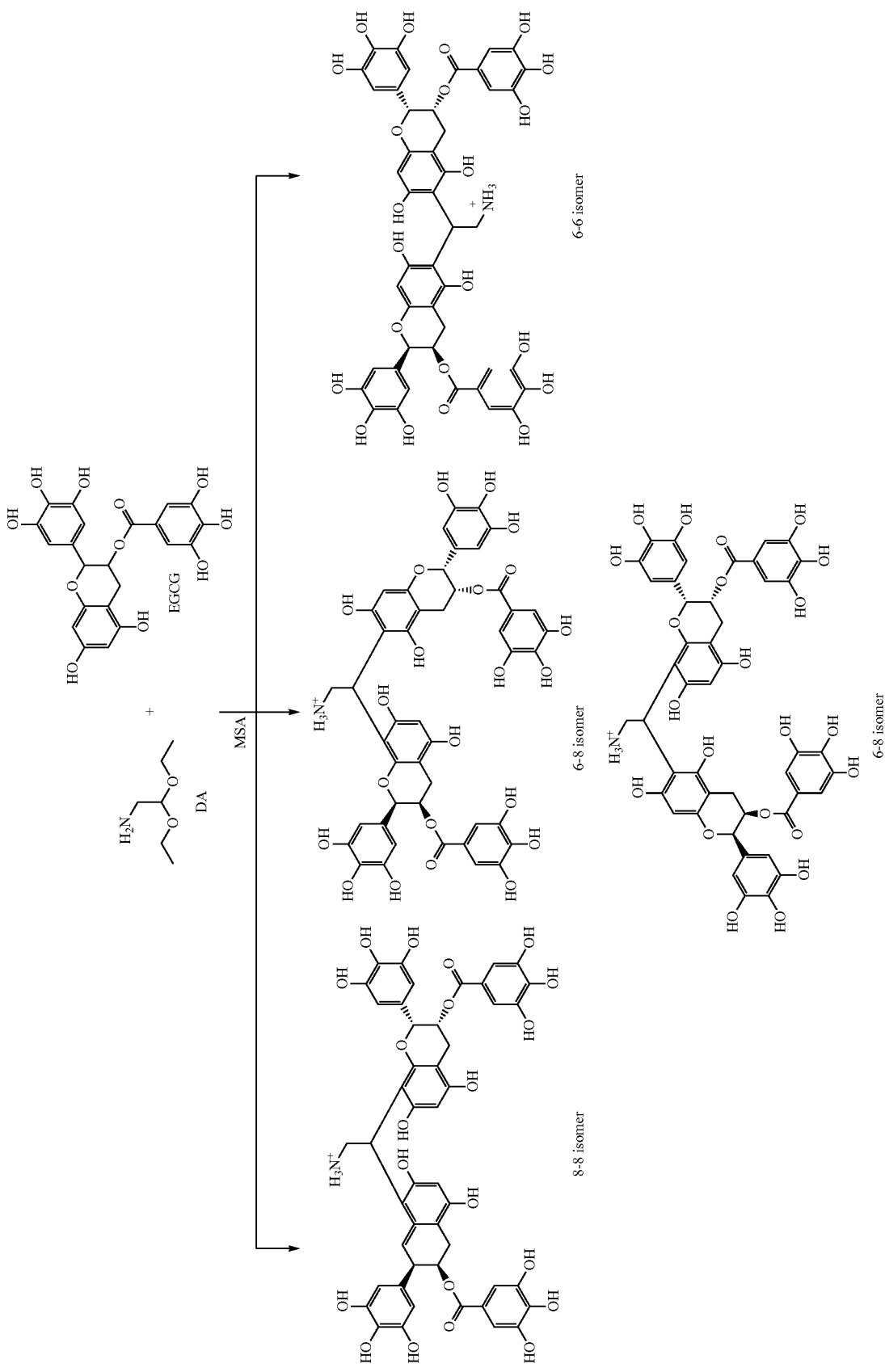

Synthesis Example 2. Preparation of Alginate-EGCG Conjugate

The EGCG dimer was conjugated to a polymer having a carboxylic acid group using a carbodiimide-mediated coupling reaction according to Scheme 2. Alginate reacted with EGCG dimer overnight at the acidic condition (pH 4.7) in the presence of N-hydroxysuccinimide (NHS), and N-(3-dimethylaminopropyl)-N'-ethylcarbodiimide (EDC) such that the amine group of EGCG and the carboxylic acid of HA were amide-bonded to prepare an alginate-EGCG conjugate.

[Scheme 2]

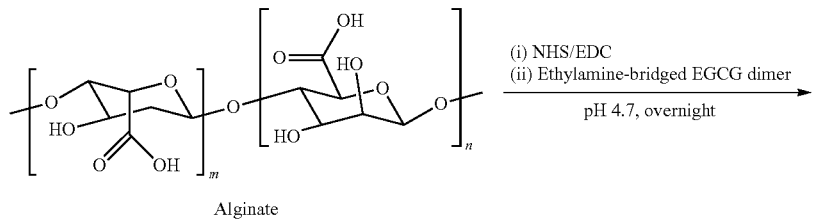

Alginate

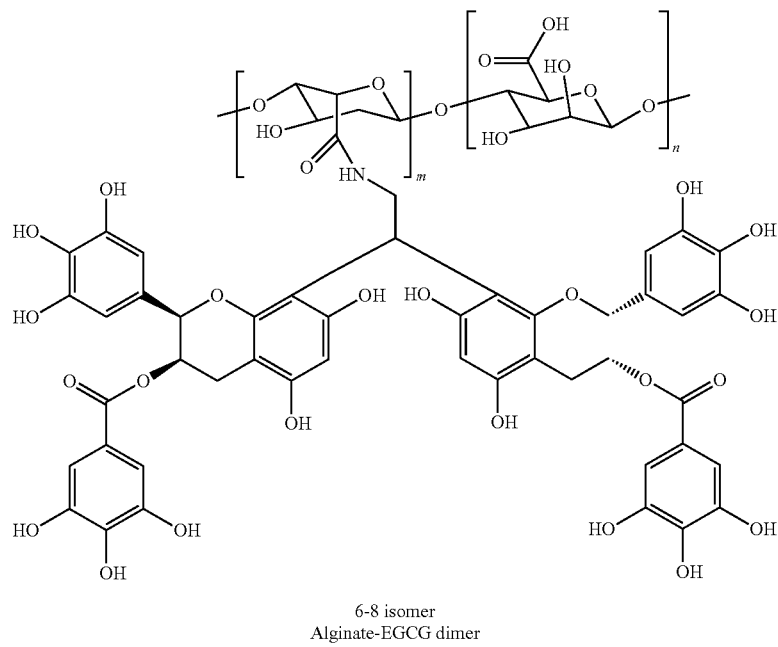

6-8 isomer
Alginate-EGCG dimer

-continued
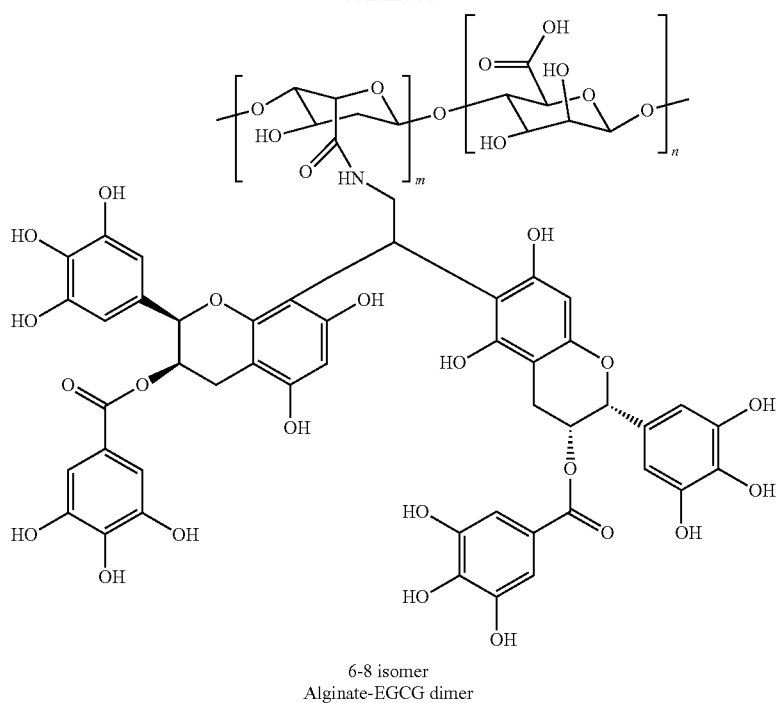
6-8 isomer
Alginate-EGCG dimer
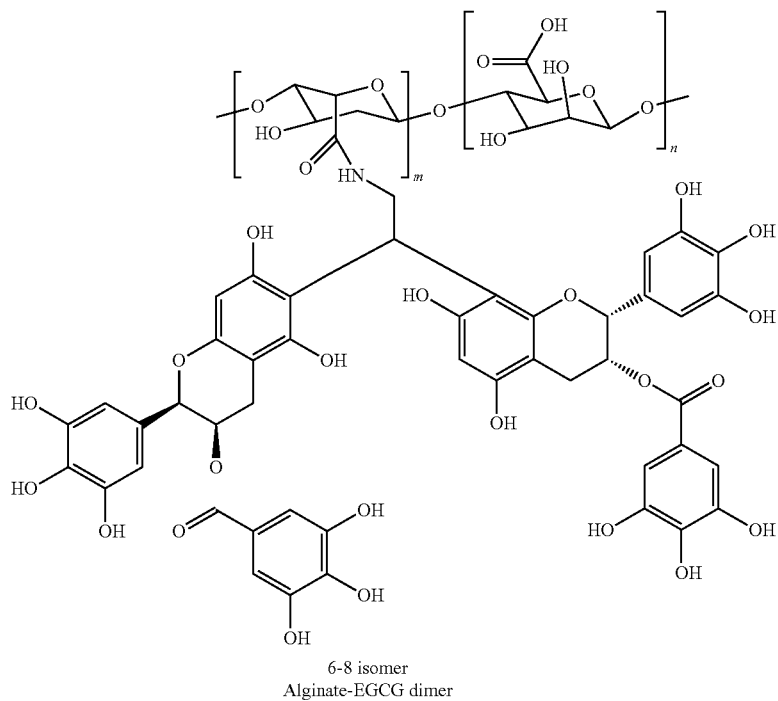
6-8 isomer
Alginate-EGCG dimer -continued

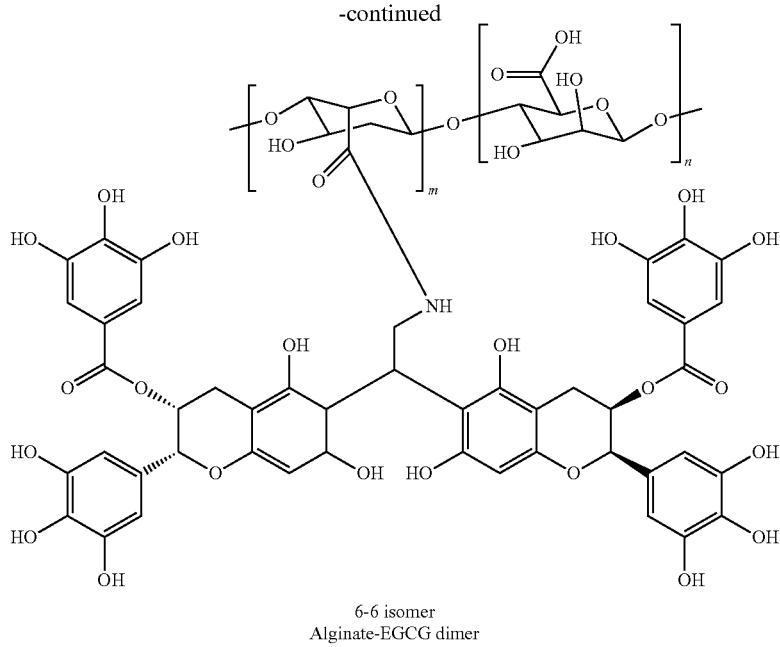

6-6 isomer
Alginate-EGCG dimer

Specifically, under dark room condition, 202 mg of alginate was added to a mixed solution of 20.2 ml of 0.4 M MES buffer (pH 5.2) and 2.5 ml of N,N-dimethylformamide (DMF) in three-necked flask, followed by stirring. When the alginate was completely dissolved, the inside of the flask was replaced with nitrogen atmosphere and the flask was sealed. After dissolving 89 mg (0.78 mmol) of NHS in 3 ml of 0.4 M MES buffer (pH 5.2) to form a mixture, it was added to the flask using a syringe. After dissolving 4 mg (0.082 mol) of EGCG dimer prepared in the Synthesis Example 1 in 2.33 ml of deionized water to form a mixture, the mixture was added to the flask using a syringe. And then, 66 mg (0.78 mmol) of EDC was dissolved in 3 ml of 0.4 M MES buffer (pH 5.2) to form a mixture, and then the mixture was added to the flask using a syringe. All reactions occurred while stirring under dark condition and nitrogen atmosphere.

And then the reaction mixture was precipitated using ethanol precipitation. Unreacted products (EDC, NHS, unreacted EGCG dimer) were removed. Specifically, under nitrogen atmosphere, the reaction mixture was dissolved in 125 ml of deionized water, and 16.7 ml of 5M aqueous sodium chloride solution was added, and the pH was adjusted to 3. After adding 310 ml of ethanol thereto, the mixture was transferred to a container for centrifugation, and was precipitated using ultracentrifugation. The supernatant was removed, and the precipitate was dissolved in 250 ml of deionized water, and 33 ml of 5M aqueous sodium chloride solution was added, and the pH was adjusted to 3. After adding 620 ml of ethanol thereto, the mixture was transferred to a container for centrifugation, and was precipitated using ultracentrifugation. The supernatant was removed, and the precipitate was dissolved in 500 ml of the deionized water. After 67 ml of 5M aqueous sodium chloride solution was added, and the pH was adjusted to 3. After adding 1,240 ml of ethanol thereto, the mixture was transferred to a container for centrifugation, and was precipitated by ultracentrifugation. The supernatant was removed, and the precipitate was dissolved in 300 ml of deionized water.

The obtained solution was dialyzed for 24 hours under nitrogen atmosphere using a 350 Da dialysis membrane. The dialyzed solution was rapidly cooled down and freeze-dried to obtain the desired alginate-EGCG (di) conjugate. The prepared alginate-EGCG (di) conjugate was stored in a cryogenic freezer before use.

Synthesis Example 3. Oxidation of EGCG Dimer

EGCG may be denatured in two main manners: oxidation and epimerization. A pattern and rate of the denaturation depend on several conditions such as the concentration of EGCG, pH, temperature, and partial pressure of oxygen. When EGCG is present at a micromolar concentration level, oxidation proceeds rapidly. When EGCG is present at a millimolar concentration level, EGCG molecules inhibit oxidation with each other, thereby lowering the oxidation rate. Further, under weakly acidic condition of pH 2 to 5.5, EGCG oxidation is suppressed but the epimerization proceeds. The EGCG oxidation proceeds rapidly under strong acid or basic conditions. Epimerization of EGCG occurs at a temperature of 50° C. or higher, but oxidation proceeds at a lower temperature than 50° C. In particular, it was identified that EGCG denaturation proceeded very slowly under cryogenic conditions. Further, as the oxygen partial pressure is lower, the oxidation of EGCG is more inhibited and rather, the epimerization proceeds. When EGCG is exposed to air in an environment where pH or concentration conditions are not met, EGCG may rapidly oxidize and form aggregates.

Therefore, in order to oxidize the EGCG dimer such that the aggregates are not formed, the concentration of EGCG, pH, temperature and oxygen partial pressure were adjusted.

The oxidation of alginate-EGCG (di) conjugate is shown below.

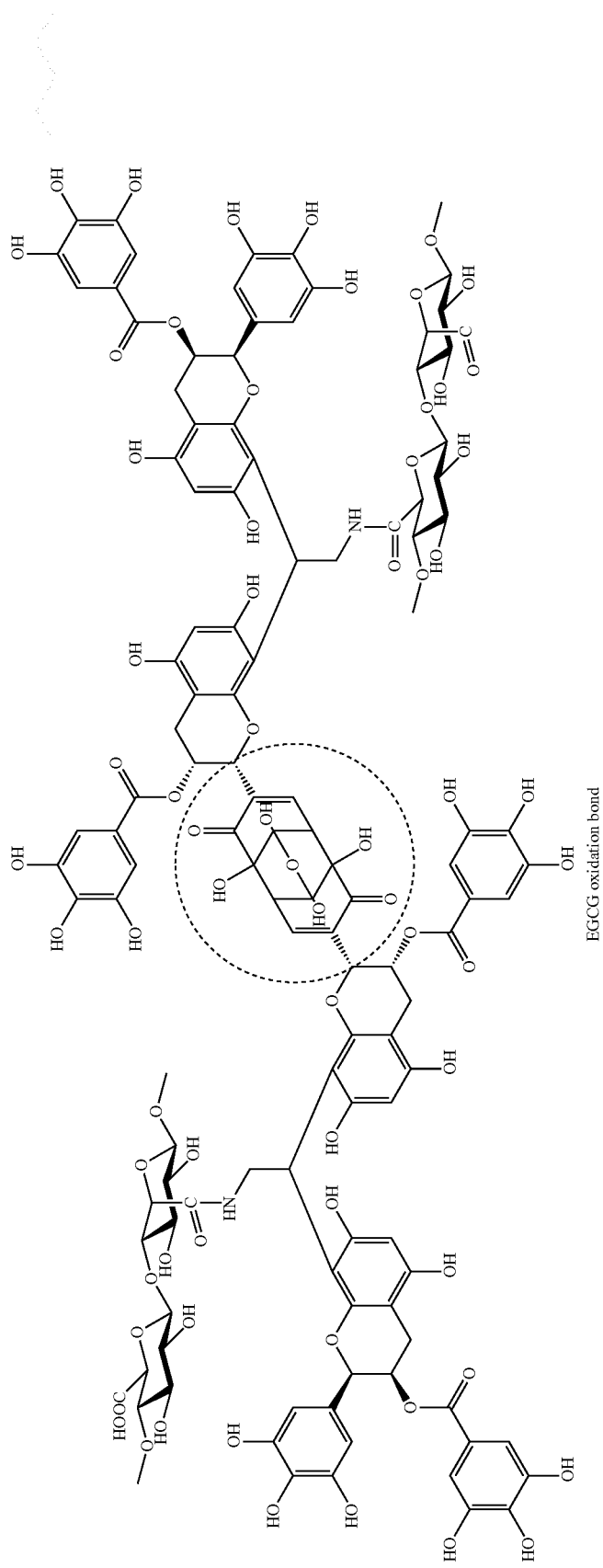

Preparation Example

Establishment of Ratio Between Alginate and EGCG Dimer Identification of Hydrogel Formation of Alginate-EGCG Conjugate In order to prepare an optimized micro-capsule for cell encapsulation, when the alginate-EGCG conjugate is exposed to the air, the alginate-EGCG conjugate should exist in a solution state while gelation thereof does not occur. To this end, the amount of EGCG compared to that of alginate was optimized while changing the type and amount of EGCG conjugated to alginate.

1. Use of EGCG Monomer

According to a conventional method, 202 mg of EGCG monomer was conjugated to alginate. Although a large amount of EGCG was conjugated to alginate, the conjugate was gelated rapidly when exposed to air even in an enzyme-free environment.

2. Use of 9 to 99 mg of EGCG Dimer

Figure 3:
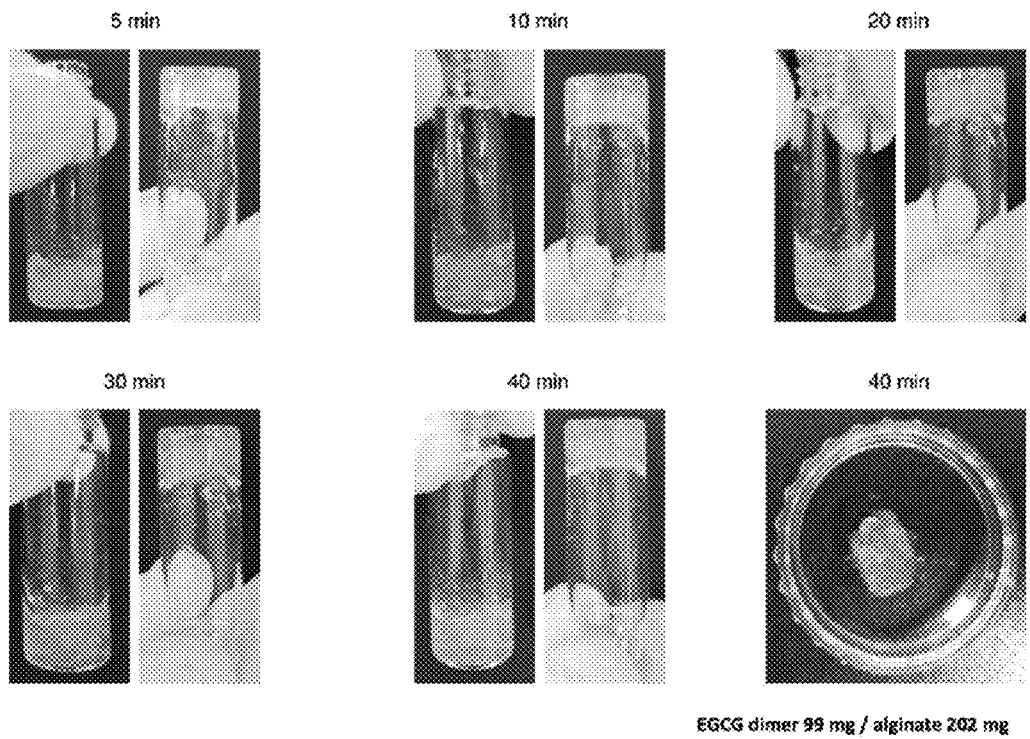
FIG. 3 shows the identification of the presence or absence of calcium ion ($Ca^{2+}$) independent hydrogel formation of alginate-EGCG (di) conjugate prepared using 99 mg of EGCG dimer over time according to the present disclosure.
Figure 4:
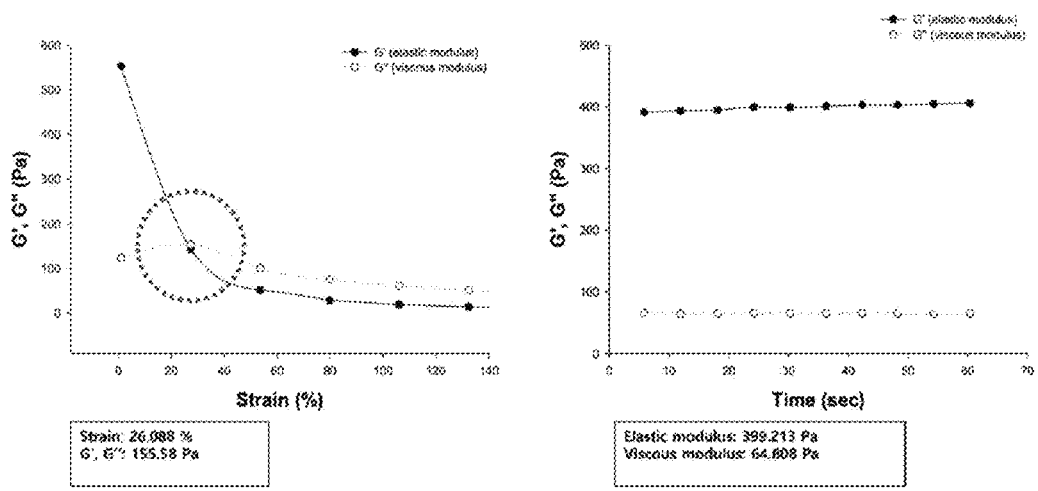
FIG. 4 is the result of measuring rheological physical properties of alginate-EGCG (di) conjugate prepared according to the present disclosure.

Alginate-EGCG conjugate was prepared by the method of Synthesis Example 2 using 99 mg of EGCG dimer. However, as shown in FIG. 3, the conjugate immediately formed a hydrogel when exposed to oxygen in the air. The rheological physical properties of the formed hydrogel were measured. The result is shown in FIG. 4. The physical properties of the formed hydrogel were at a level such that the hydrogel was applicable to micro-capsules. However, the gelation occurred immediately upon exposure thereof to air. Thus, it was difficult to apply the conjugate to the micro-capsule process. Therefore, there was a need to reduce the amount of EGCG dimer conjugated to alginate.

3. Use of 4 mg of EGCG Dimer

Figure 5:
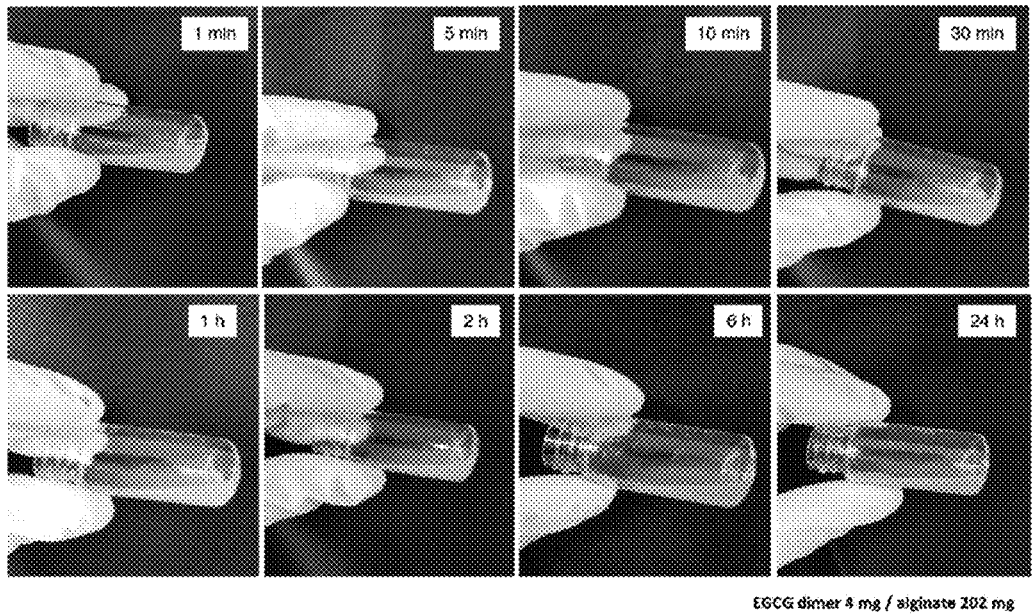
FIG. 5 shows the identification of the presence or absence of calcium ion ($Ca^{2+}$) independent hydrogel formation of alginate-EGCG (di) conjugate prepared using 4 mg of EGCG dimer over time according to the present disclosure.

Alginate-EGCG conjugate was prepared by the method of Synthesis Example 2 using 4 mg of EGCG dimer. The prepared conjugate was not gelated when exposed to air. This is shown in FIG. 5.

Preparation of Micro-Capsule

Comparative Example 1. Calcium-Alginate Capsule Preparation

Calcium-alginate capsules were prepared according to a known preparation method.

Comparative Example 2. Alginate-EGCG (Mono) Micro-Capsule Preparation

Alginate-EGCG (mono) micro-capsule was prepared using 202 mg of EGCG monomer.

Comparative Example 3. Alginate-EGCG (Di) Micro-Capsule Preparation

The micro-capsule was prepared using alginate-EGCG (di) conjugate prepared using 4 mg of EGCG dimer. During the capsule preparation, the concentration of calcium ion was 100 mM or 1 M.

Figure 6:
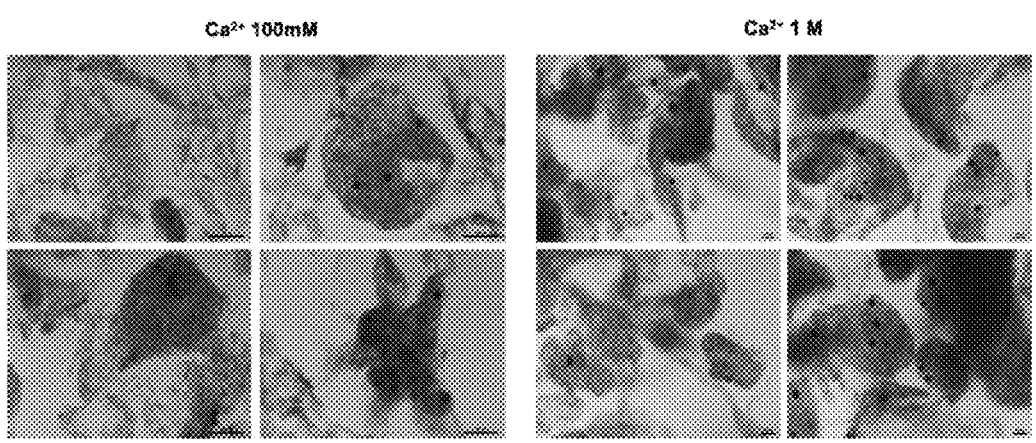
FIG. 6 is the result of alginate-EGCG (di) micro-capsule preparation according to Comparative Example 3 according to the present disclosure.

As shown in FIG. 6, the capsule was not formed reliably. In the encapsulating processes, this unreliable formation generally occurs when the alginate concentration is out of the appropriate range or the calcium ion concentration is low. In accordance with the present disclosure, it was found that the antioxidant properties of EGCG inhibit calcium ion-mediated alginate crosslinking. In general, catechins such as EGCG may bind with metal cations and thus may be chelated. It is believed that A small amount of calcium ions present in the reaction product combines with EGCG to change the structure of EGCG and reduce the antioxidant activity of EGCG.

Comparative Example 4. Alginate/Alginate-EGCG (Di) Micro-Capsule Preparation

In order to solve the crosslinking inhibition problem by EGCG, the encapsulating was performed using a mixture of pure alginate solution and alginate-EGCG (di) conjugate. The reaction was carried out in a dark room condition and under nitrogen atmosphere in order to prevent the oxidation of EGCG.

Figure 7:
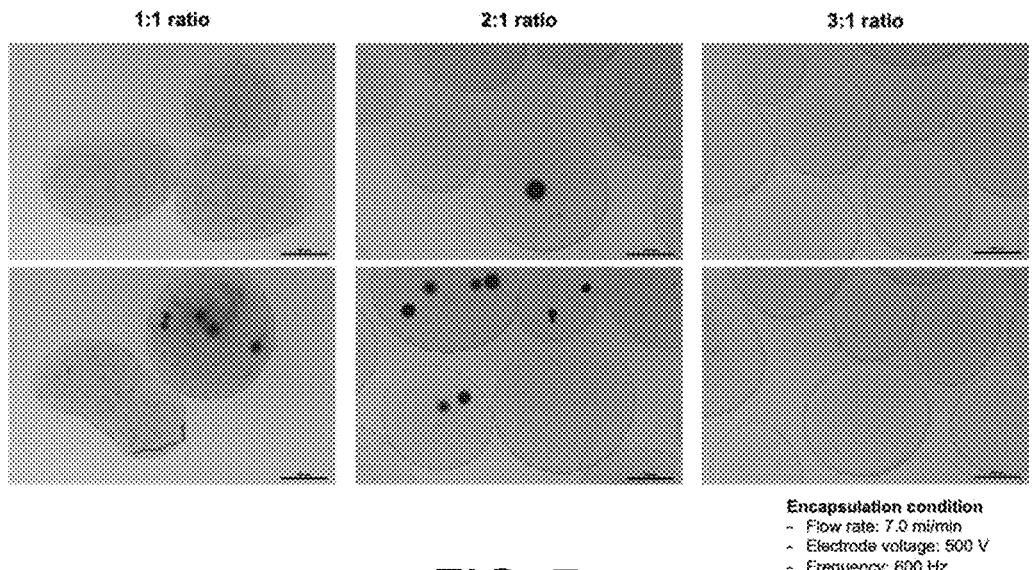
FIG. 7 is the result of alginate/alginate-EGCG (di) micro-capsule preparation according to Comparative Example 4 according to the present disclosure.

First, in order to optimize the mixing ratio between alginate and the alginate-EGCG conjugate, mixtures in which the mixing ratio between alginate and the alginate-EGCG conjugate was 1:1, 2:1 and 3:1 based on parts by weight, respectively, were prepared. The encapsulating was executed using the mixtures. As shown in FIG. 7, the micro-capsule was normally formed when the content of the alginate relative to 1 part by weight of the alginate-EGCG conjugate was 2 parts by weight or more.

Calcium Ion Dependence and Decomposition Evaluation

Figure 8:
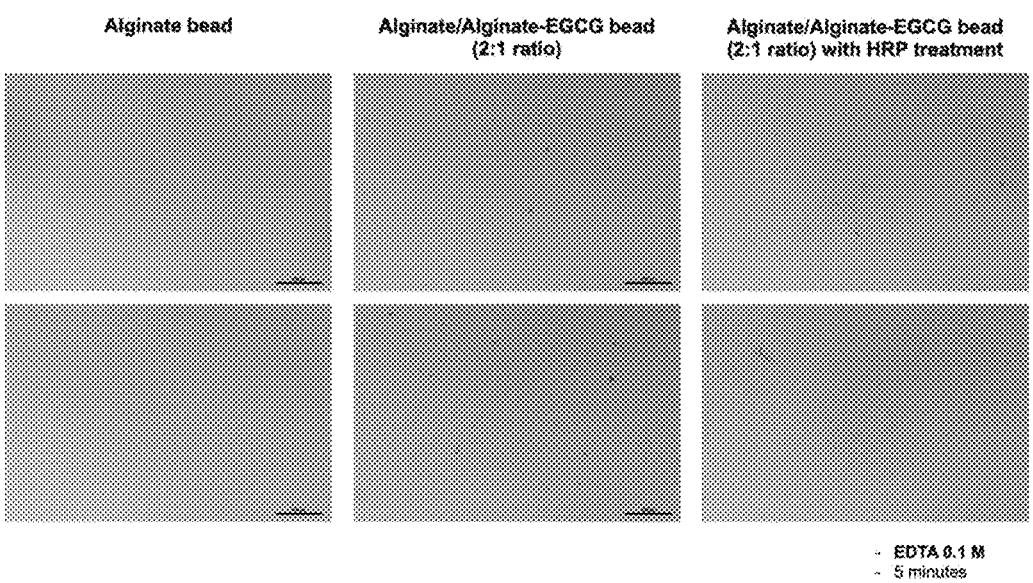
FIG. 8 shows the evaluation of the degree of decomposition when treating micro-capsules according to Comparative Example 1 and Comparative Example 4 with a calcium ion chelating agent for 5 minutes (a: Comparative Example 1, b: Comparative Example 4).

Calcium ion dependence and decomposition of the micro-capsules prepared according to Comparative Example 1 and Comparative Example 4 (micro-capsules of mixtures of alginate and alginate-EGCG conjugate) were evaluated. Specifically, after the capsules were subjected to treatment with EDTA as a calcium ion chelating agent, the shape of the micro-capsule was identified. The result is shown in FIG. 8.

It was identified that the micro-capsule of Comparative Example 4 was more resistant to the calcium ion chelating agents than the micro-capsule of Comparative Example 1 was. However, it was found that the decomposition did not have a big difference therebetween, and thus the effect of improving the decomposition was not significant. On the other hand, when the capsule was subjected to the HRP enzyme treatment, the micro-capsule of Comparative Example 4 was degraded faster than that of Comparative Example 1. This was believed to be due to the EDTA catalysis of the remaining HRP.

Example 1. Preparation of Surface-Modified Alginate Micro-Capsule

The calcium-alginate micro-capsule was surface-modified with an EGCG dimer. The micro-capsules were prepared while the conditions such as various reaction times, EGCG dimer concentration, and the absence or presence oxidation treatment were controlled for optimization.

Reaction Time

In order to increase the amount of conjugated EGCG thereto without increasing the gelation tendency, the calcium-alginate capsule was prepared, and then the EGCG dimer was conjugated thereto.

The calcium-alginate capsule was prepared by a known method. The prepared capsule was washed 4 times with HEPES buffer (pH 7.4). And then the capsule was washed twice with MES buffer (pH 6.0). The washed capsule was stored in 50 ml of MES buffer. Under dark conditions, 40 mg (0.347 mmol) of NHS dissolved in 2 ml of MES buffer was added to the MES buffer in which capsules were present, followed by stirring. Next, EGCG dimer was added thereto at various concentrations (0.347 mmol and 0.174 mmol), followed by stirring. Next, 66 mg (0.0347 mmol) of EDC dissolved in 2 ml of MES buffer was added. The reaction mixture was identified over time (10 minutes, 20 minutes, 30 minutes and 60 minutes) to check the surface-modified state. All reactions were carried out under dark room conditions.

Further, in order to identify the effect of the oxidation treatment, 1 U/ml of HRP was added thereto at a reaction time of 0 minutes, followed by stirring for 30 minutes.

At this time, the amounts of EDC and NHS used in the reaction were controlled so that the molar ratio of EDC:NHS:alginate=1:1:1 based on the number of moles of the unit of alginate.

Figure 9:
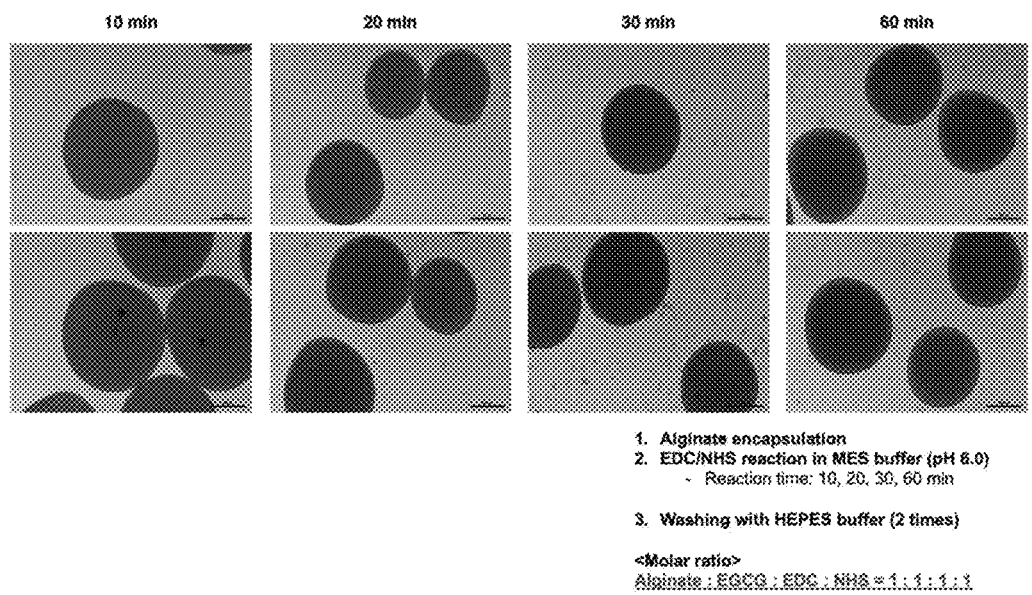
FIG. 9 is the micro-capsule preparation result of Example 1 based on the reaction time according to the present disclosure.

As shown in FIG. 9, the surface modification of the alginate capsule was performed normally at the reaction times of 10, 20, 30 and 60 minutes. As the reaction time increased, more aggregation of EGCG was formed and another EGCG dimer was bonded to the EGCG dimer bonded to the micro-capsule surface, and EGCG penetrated into the micro-capsule.

Figure 10:
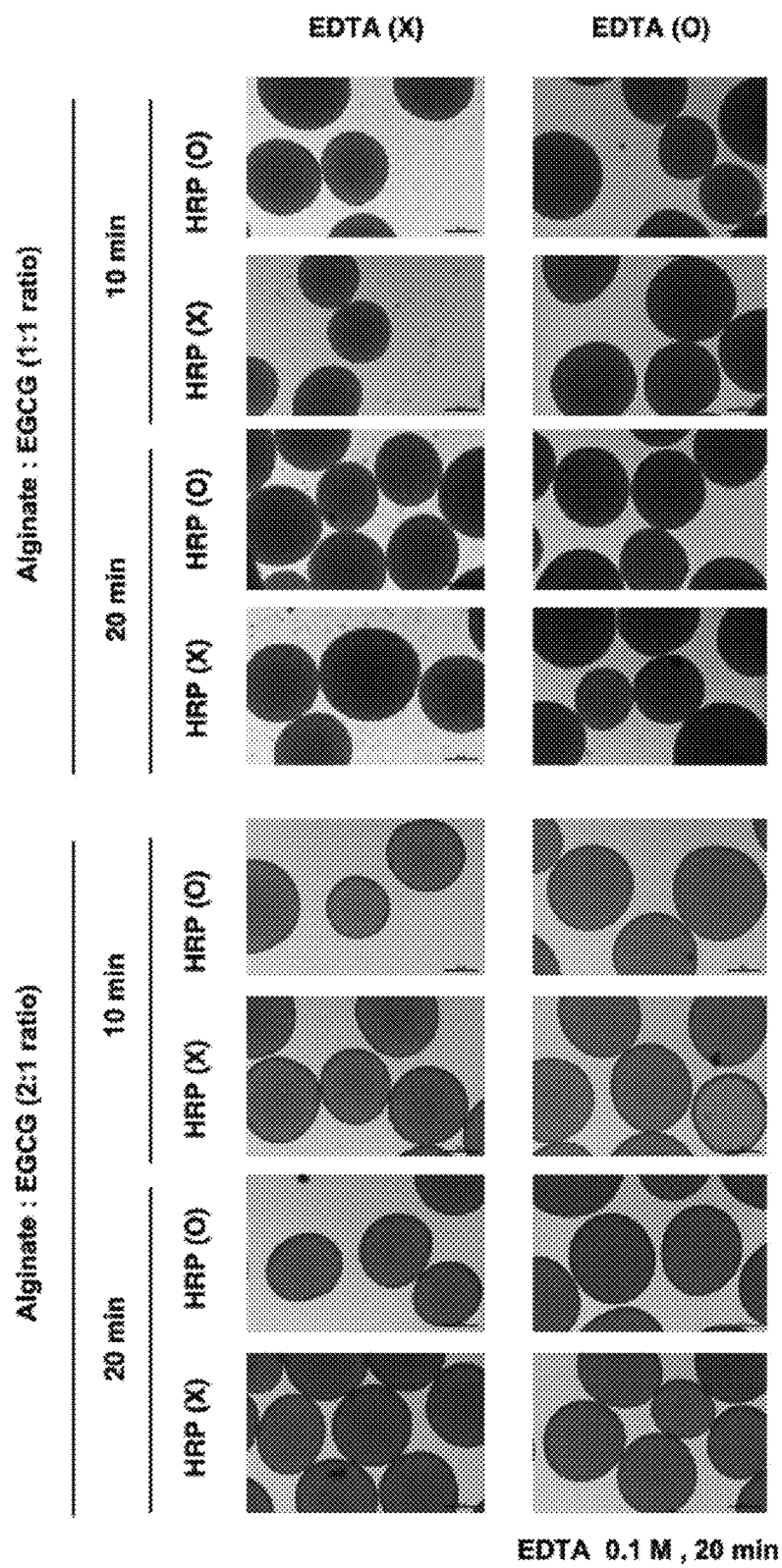
FIG. 10 is the micro-capsule preparation result of Example 1 based on the presence or absence of HRP treatment, various reaction times, and EGCG dimer concentrations.

In additional experiments, in order to minimize cell damage, the reaction time was set to 10 to 20 minutes. Reaction Time, EGCG Dimer Concentration and HRP Treatment The micro-capsule was surface-modified with or without HRP treatment, for various reaction times and at EGCG dimer concentration. An image of the surface modification is shown in FIG. 10.

The degree of binding of EGCG was found to be more influenced by the concentration of the EGCG dimer rather than by the reaction time.

Figure 11:
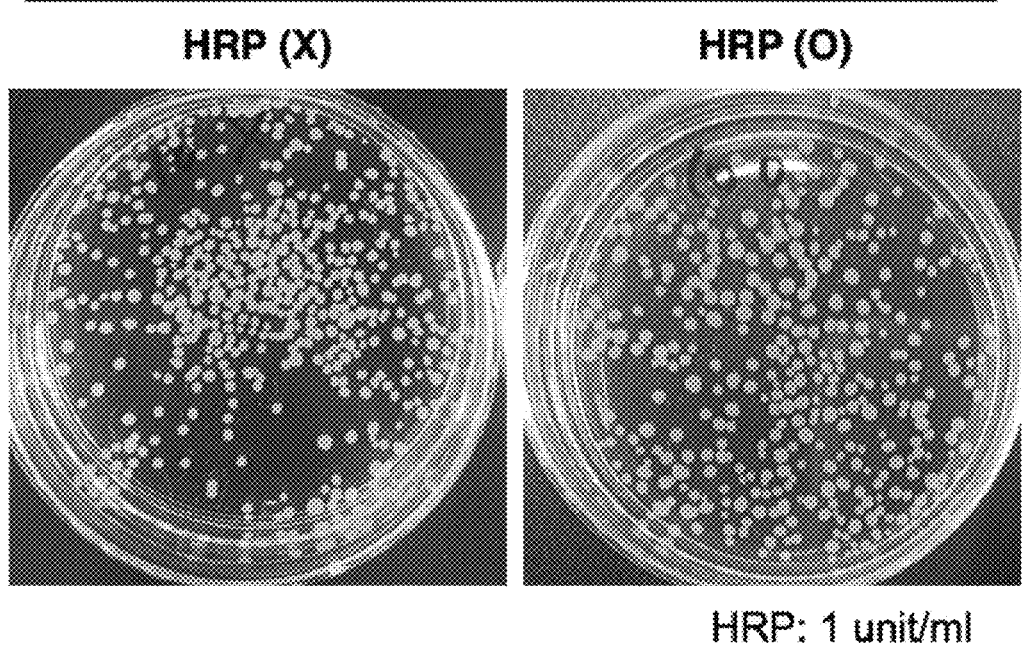
FIG. 11 shows the result of identifying the color change of the surface-modified alginate micro-capsule with or without HRP treatment (left: HRP absence, right: HRP added).
Figure 12:
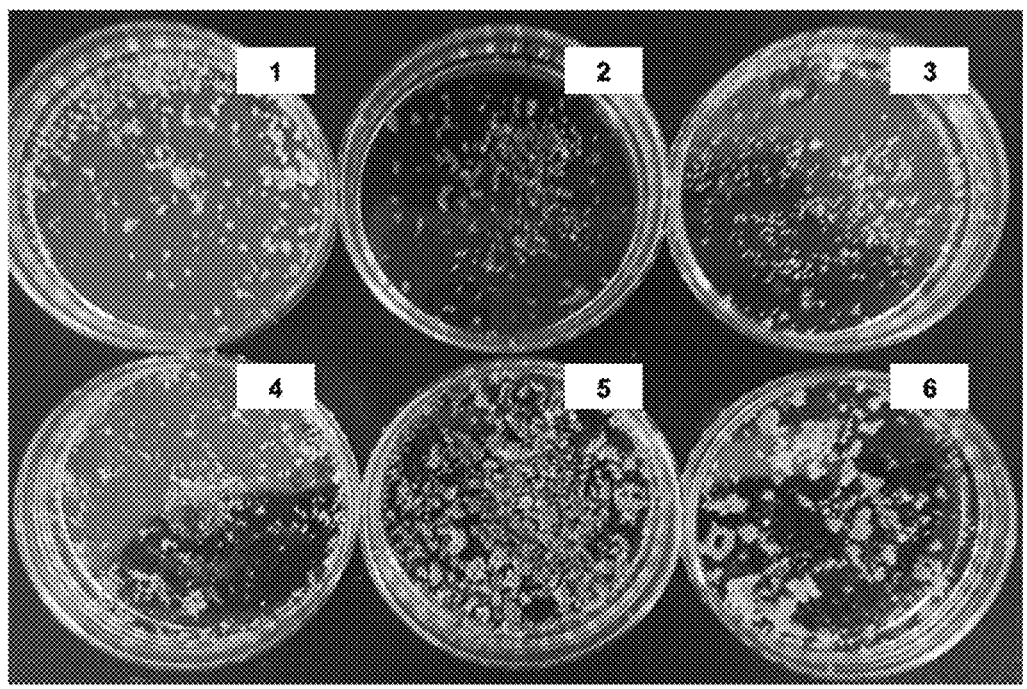
FIG. 12 shows the result of identifying between EGCG-conjugated alginate bead, alginate bead, and alginate-EGCG bead based on whether HRP is added and whether AC alginate is coated.

Further, oxidation was not significantly observed with an optical microscope, but was easily observed via color change with the naked eye. FIG. 11 and FIG. 12 are the results of identifying the color change of the surface-modified alginate micro-capsule with or without HRP treatment. In FIG. 11, the left side shows that the HRP is not added and the right side shows that the HRP is added. As the EGCG on the micro-capsule surface was oxidized by HRP, EGCG aggregated with each other, and thus turned red.

Example 2. Surface-Modified Alginate Capsule Preparation Process and Alginate Coated Surface-Modified Alginate Micro-Capsule Preparation The EGCG dimer contains an amine group. The EGCG dimer directly conjugated with alginate is not positively charged because the amine group forms an amide bond with the alginate. However, the EGCG dimer formed via oxidation between EGCGs has an amine group and thus has the positive charge. According to conventional studies, positively charged biomaterials induce more immune responses and inflammation than neutral or negatively charged biomaterials induce.

To prevent the occurrence of unnecessary immune responses, alginate was coated on an outer face of the surface-modified alginate micro-capsule of Example 1.

The calcium-alginate capsule was prepared by a known method and the prepared capsule was washed 4 times with HEPES buffer (pH 7.4), and next, was washed twice with MES buffer (pH 6.0). The washed capsule was stored in 50 ml of MES buffer. Under dark conditions, 40 mg (0.347 mmol) of NHS dissolved in 2 ml of MES buffer was added to the MES buffer in which capsules were present, followed by stirring. Next, EGCG dimer was added thereto at various concentrations (0.347 mmol and 0.174 mmol), followed by stirring. Next, 66 mg (0.0347 mmol) of EDC dissolved in 2 ml of MES buffer was added thereto. The reaction mixture was identified over time (10 minutes, 20 minutes, 30 minutes and 60 minutes) to check the surface-modified state. All reactions were carried out under dark conditions.

Further, in order to identify the effect of oxidation treatment, a case where HRP was added thereto and a case where HRP was not added thereto were compared to each other.

Example 3. Preparation of Surface-Modified Alginate Micro-Capsule as Treated with EDTA The micro-capsules of Example 1 and Example 2 were treated with 100 mM EDTA (10 and 20 minutes) to form hollows in the micro-capsule.

Test Example 1. Structure Analysis

Surface Analysis

Figure 13:
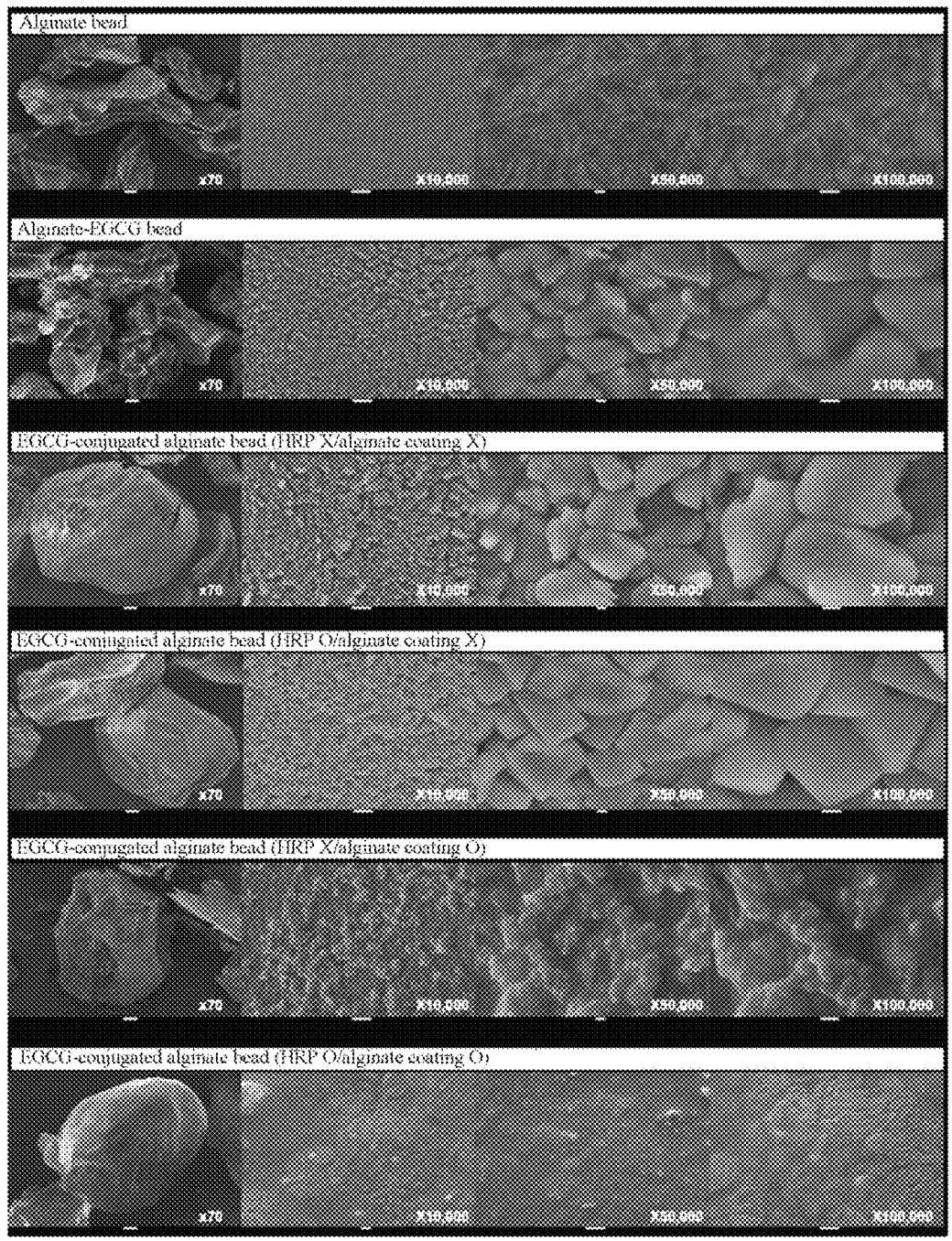
FIG. 13 is a scanning electron microscope (SEM) image of each of the micro-capsules of Comparative Example 1, Example 1, and Example 2.

FIG. 13 shows the micro-capsules of Comparative Example 1, Example 1, and Example 2 as observed with a scanning electron microscope (SEM). The SEM images were taken at ×70, ×10000, ×50000, ×100000 magnifications, respectively. Compared with Comparative Example 1, the micro-capsule of Example 1 was observed to have a specific shape on the surface thereof. On the other hand, it was identified that the specific shape as shown in Example 1 disappeared on the micro-capsule surface of Example 2. Thus, it was identified that the alginate micro-capsule as surface-modified with the EGCG dimer was coated with alginate.

Internal Structure Analysis

Figure 14:
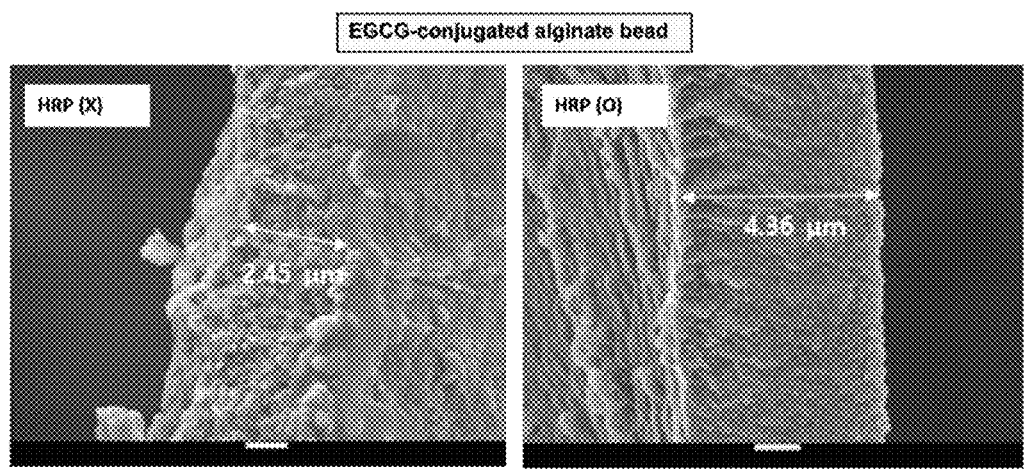
FIG. 14 is an optical microscope image of each of a micro-capsule in which HRP is absent in EGCG-conjugated alginate bead (left) and a micro-capsule in which HRP is added to the EGCG-conjugated alginate bead (right).

The internal structure of each of the micro-capsules of Example 1 and Example 2 was analyzed with a scanning electron microscope (SEM). The result is shown in FIG. 14.

It may be identified based on the SEM image that the core-shell structure was formed. The shell thickness of the HRP-treated micro-capsule was larger than that of the HRP non-treated micro-capsule, and the former had a larger number of pores than the latter.

Figure 15:
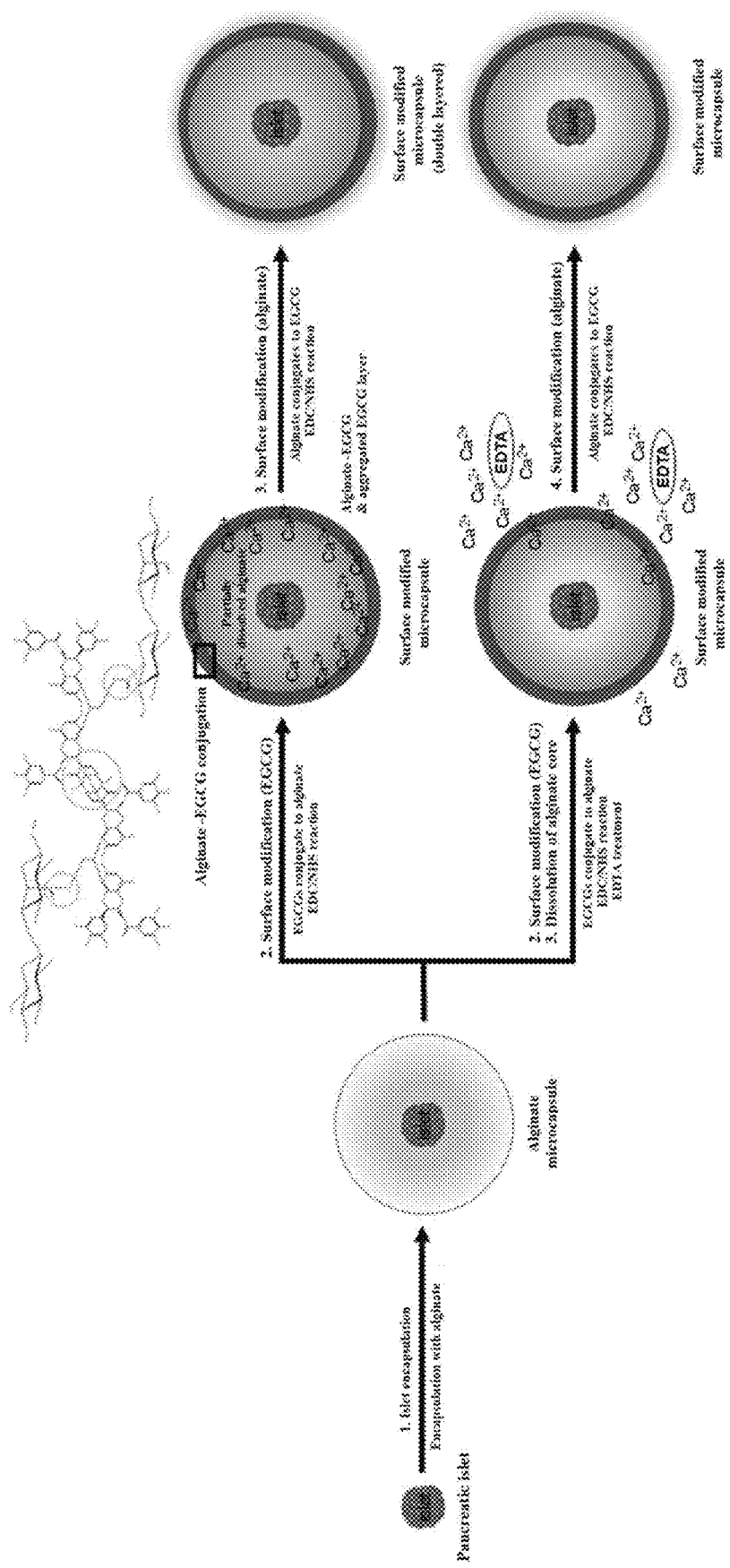
FIG. 15 schematically shows the encapsulation process of an islet with a surface-modified alginate micro-capsule according to Example 1 or 2.

FIG. 15 schematically shows the encapsulation process of the islet with the surface-modified alginate micro-capsule according to Example 1 or 2.

First, the islet was encapsulated with the calcium-alginate micro-capsule. Next, the EGCG dimer was bonded to the surface of the calcium-alginate micro-capsule. Because the EGCG dimer combined with alginate chelated the calcium therein, the calcium-alginate hydrogel was dissolved. In this process, the inner alginate was partially dissolved to form a micro-capsule having an alginate core/alginate-EGCG dimer shell structure. At this time, the dissolution of the calcium-hydrogel may occur in whole or only partially.

This structure may improve the viability of the encapsulated islet because this structure allows the oxygen and nutrients to be easily diffused than the micro-capsule according to the prior art does.

Calcium Ion Dependence and Decomposition Evaluation

The calcium ion dependence and decomposition of each of the micro-capsules of Comparative Example 1 and Example 1 based on the content of the EGCG dimer, reaction time, and HRP treatment were evaluated. The micro-capsule of each of Comparative Example 1 and Example 1 was treated with EDTA (100 mM) known as a calcium ion chelating agent, and morphological changes thereof were identified.

Figure 16:
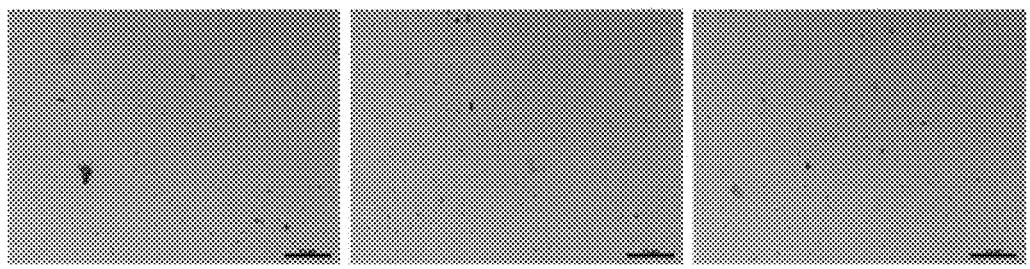
FIG. 16 identifies a change in shape after the calcium-alginate micro-capsule of Comparative Example 1 is treated with EDTA (100 mM), which is known as a calcium ion chelating agent, for 20 minutes.
Figure 17:
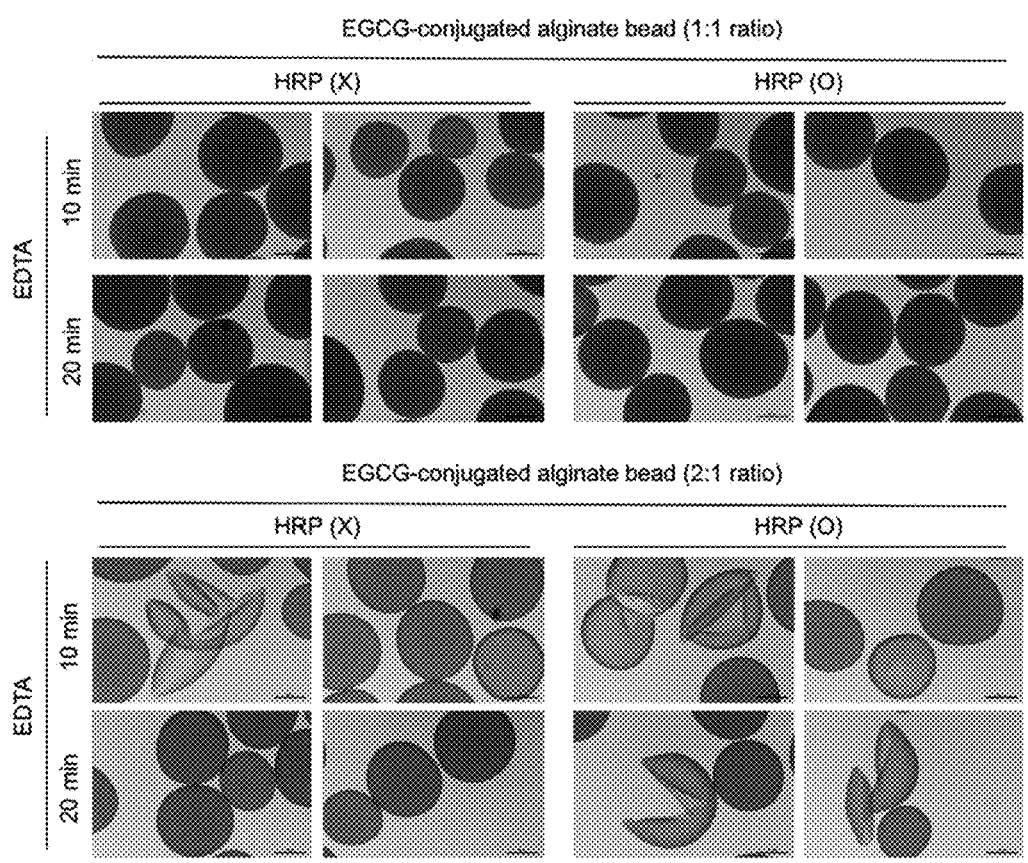
FIG. 17 identifies a change in shape after the micro-capsule of Example 1 is treated with EDTA (100 mM), known as a calcium ion chelating agent, for 10 or 20 minutes.

As shown in FIG. 16, the calcium-alginate micro-capsule of Comparative Example 1 was completely decomposed under the condition of treatment with 100 mM EDTA for 20 minutes and turned into a solution. On the other hand, as shown in FIG. 17, the micro-capsule of Example 1 did not collapse during EDTA treatment. The shape thereof was maintained. This means that the micro-capsule according to the present disclosure has resistance to the calcium ion chelation by EDTA. The EDTA treatment allows the formation of the hollows in the micro-capsule of Example 1, thereby providing an advantage in terms of the diffusion of the material into and the oxygen supply into the capsule. The physical properties (stability against physical damage) thereof of the EDTA-treated micro-capsule were superior to those of the EDTA-untreated micro-capsule.

On the other hand, as the amount of EGCG dimer used in micro-capsule preparation increased and the reaction time was longer, the degree of degradation tended to increase, but was not a significant level. Further, the degree of decomposition of the HRP-treated micro-capsule of Example 1 was increased. This seems to be due to the fact that the remaining HRP increases the activity of EDTA.

Therefore, adjusting the treatment time and concentration of EDTA to optimize the shape of the micro-capsule may allow the survival of the encapsulated islet to be further improved and allow the encapsulated islet to be protected against physical damage.

Evaluation of Rheological Properties

In order to identify the physical properties of micro-capsules according to Comparative Example 1, Comparative Example 3 and Example 1, rheological properties thereof were measured. The results are shown in FIG. 18 to FIG. 21.

Figure 18:
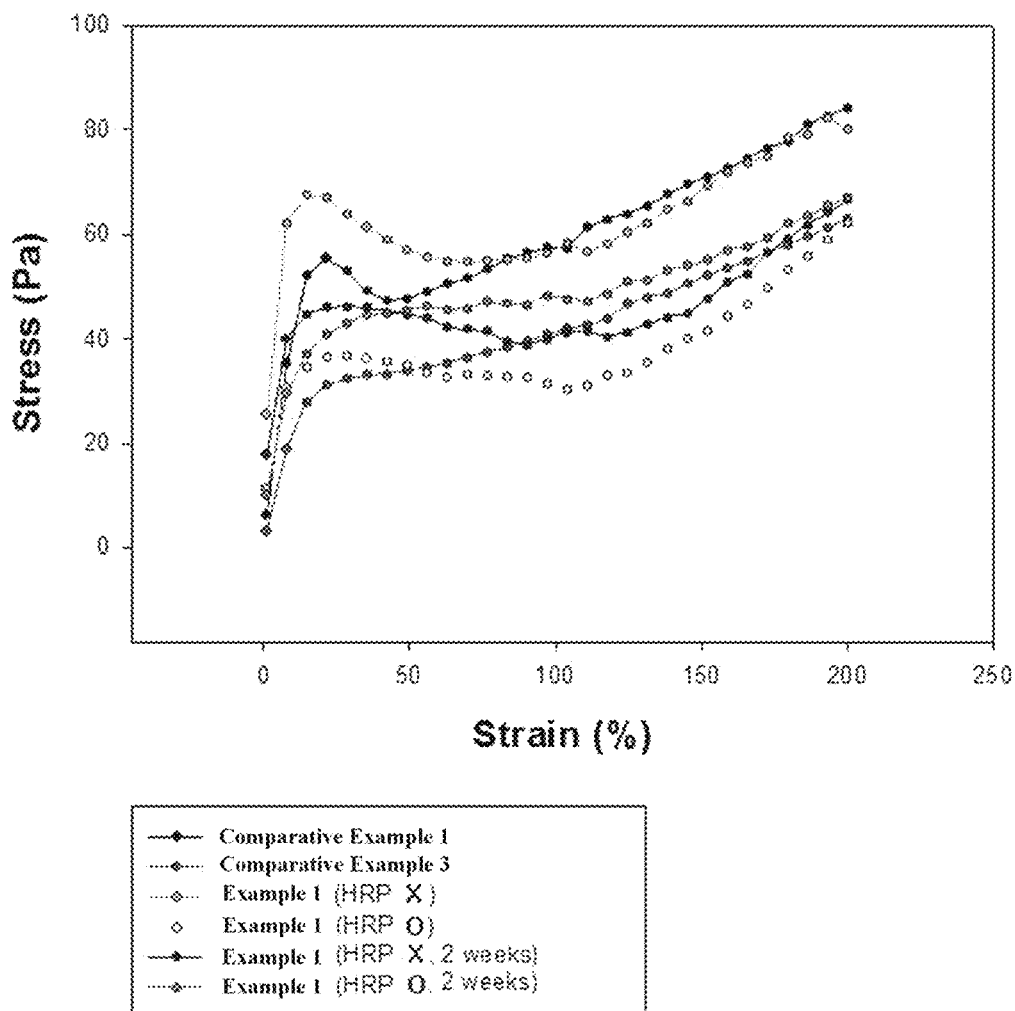
FIG. 18 shows the rheology measurement results of micro-capsules according to Comparative Example 1, Comparative Example 3, and Example 1.
Figure 19:
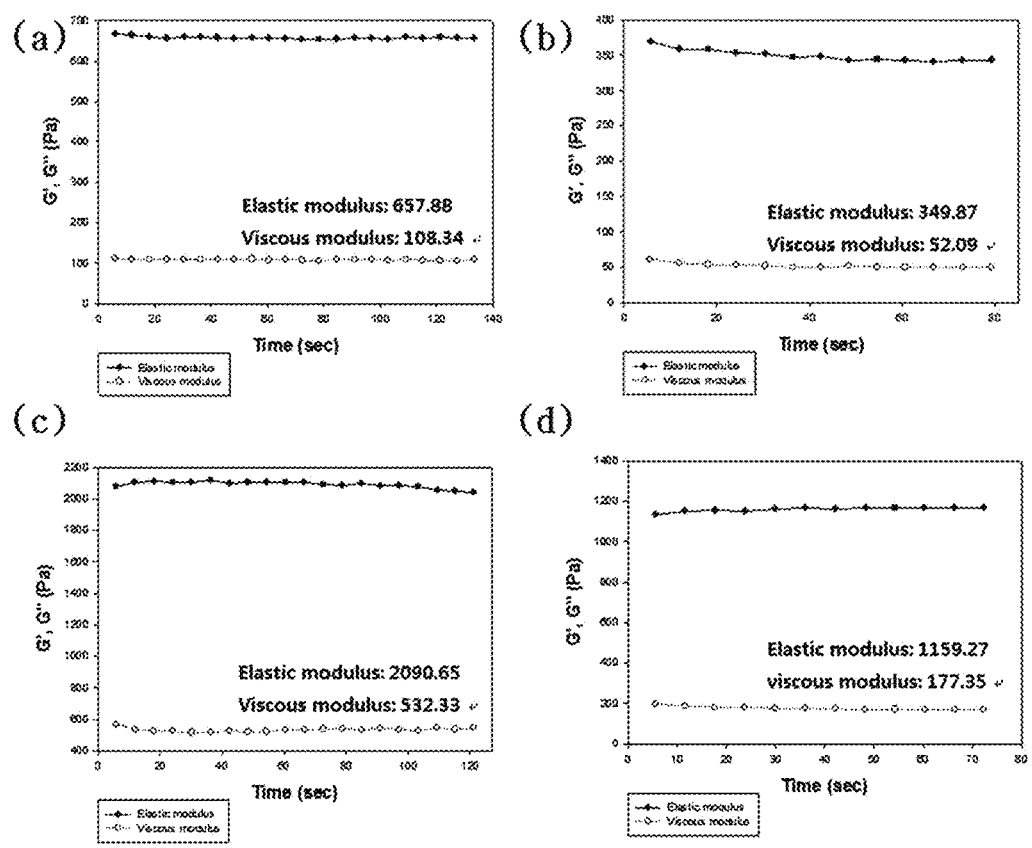
FIG. 19 shows the results of measuring the viscoelasticity of micro-capsules according to Comparative Example 1, Comparative Example 3, and Example 1: (a) Comparative Example 1, (b) Comparative Example 3, (c) Example 1, HRP added, and (d) Example 1, HRP absent.
Figure 20:
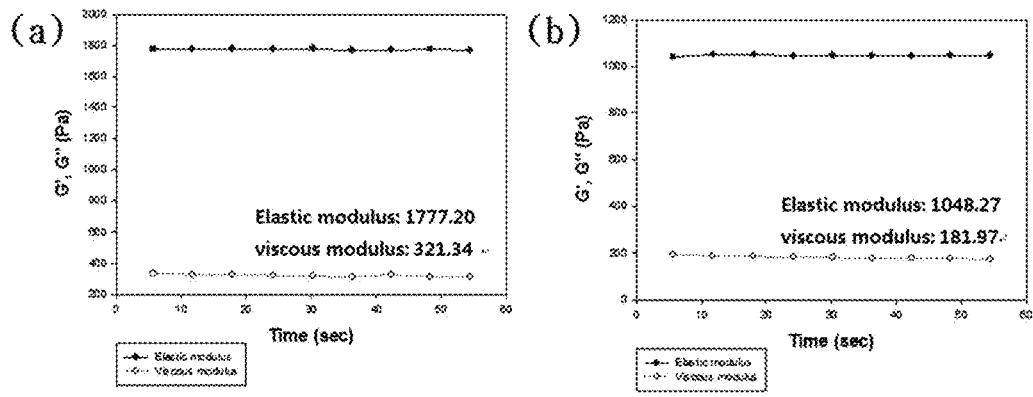
FIG. 20 is the viscoelasticity measurement results in 2 weeks after the preparation of micro-capsules according to Example 1: (a) HRP added, and (b) HRP absent.
Figure 21:
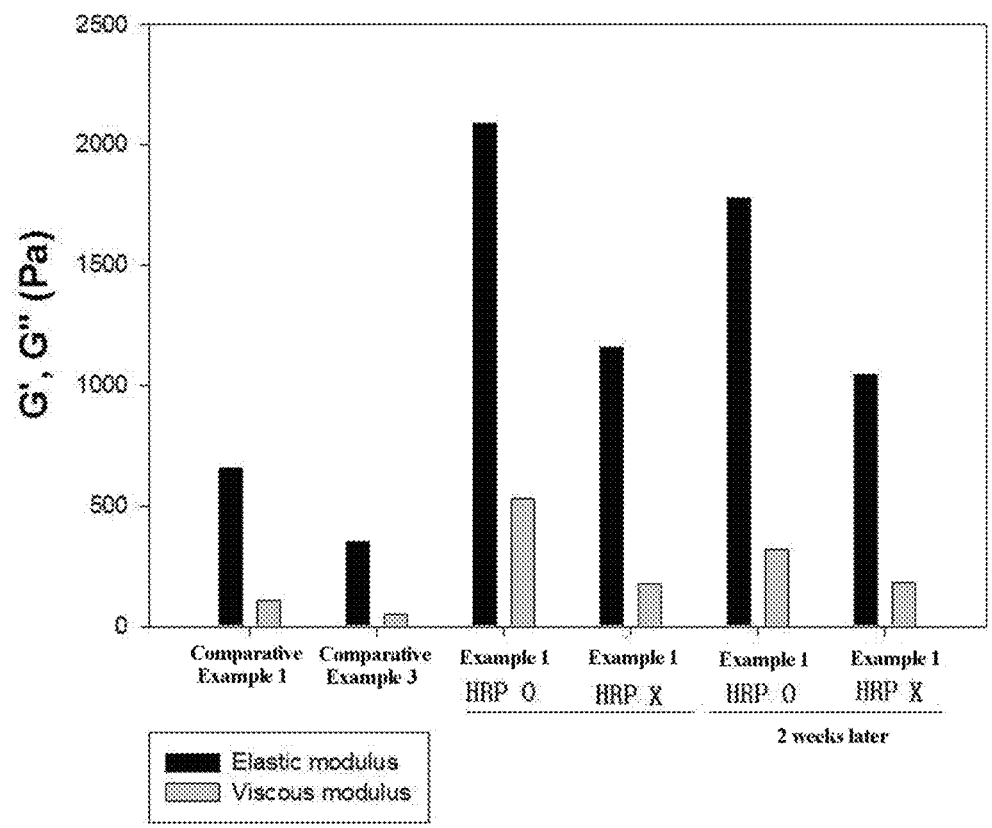
FIG. 21 shows the results of measuring the viscoelasticity of micro-capsules according to Comparative Example 1, Comparative Example 3, and Example 1.

FIG. 18 is the rheology measurement result, and FIGS. 19 to 21 are viscoelastic measurement results.

Referring to FIG. 19, the micro-capsule of Comparative Example 3 showed lower physical properties compared to Comparative Example 1. This is presumed to be due to the calcium ion chelating action of EGCG. The micro-capsule of Example 1 exhibited higher physical properties than the micro-capsule of Comparative Example 1 regardless of the presence or absence of HRP treatment. On the other hand, the HRP-treated micro-capsule showed lower physical properties than the HRP non-treated micro-capsule. This means that despite the fact that a thicker EGCG shell was formed due to the HRP treatment, the physical properties of the core were reduced because the calcium ion chelating action of EGCG acted more actively due to the HRP treatment.

After preparing the micro-capsule of Example 1 and storing the same for 2 weeks, changes in viscoelasticity thereof were identified (FIG. 21). The viscoelasticity of the HRP-treated micro-capsule was decreased, while the viscoelasticity of the HRP non-treated micro-capsule was substantially maintained. This is because in the HRP-treated micro-capsule, the dissolution of alginate in the core was promoted to partially reduce physical properties thereof, but stable bonds between EGCGs were formed via HRP treatment. On the other hand, in the case of HRP non-treated micro-capsules, high physical properties thereof were observed due to the alginate of the core, which was not completely dissolved, at the time of preparation. However, during the storage thereof, the alginate of the core was dissolved, thereby to reduce the physical properties thereof.

Example 4. Islet Encapsulating

The islet was encapsulated using the micro-capsule preparation method according to Example 1.

During the micro-capsule preparation, the characteristics of the capsule based on the presence or absence of HRP treatment were identified with an optical microscope. The result is shown in FIG. 22.

A top of FIG. 22 is an optical microscope image of an islet encapsulating surface-modified alginate micro-capsule without the HRP treatment. A bottom of FIG. 22 is an optical microscope image of the islet encapsulating surface-modified alginate micro-capsule having the HRP added thereto. A portion of the alginate in the core was dissolved in the form of a solution, while a remaining portion thereof was observed in the form of a slurry having a hydrogel state. It was identified that the encapsulation of islet was well performed to improve viability while protecting cells from physical damage.

Example 5. Identification of Resistance to Decomposition of Surface-Modified Micro-Capsules Based on EGCG Content In order to identify resistance to the decomposition of surface-modified micro-capsules based on the EGCG content, the micro-capsule forms at 10.5, 21, 42 and 84 mg of EGCG per 5 ml of alginate were identified with an optical microscope and are shown in FIG. 23. The resistance to decomposition that occurs when $Ca^{2+}$ is removed via EDTA treatment was measured. It was identified that resistance thereto appeared from when the EGCG content was 84 mg or more per 5 ml of alginate.

Example 6. Identification of Formation of Outer EGCG Layer of Surface-Modified Micro-Capsule Based on EGCG Content In order to identify the formation of the outer EGCG layer of the surface-modified micro-capsule based on the EGCG content, each of the shapes of the outer layers when the amount of EGCG was 10.5, 21, 42 and 84 mg was identified with a confocal optical microscope and was shown in FIG. 24. The resistance to decomposition was achieved due to the EGCG layer formed outside the core alginate. The bonds inside the EGCG layer are formed due to autooxidation of EGCG itself irrespective of $Ca^{2+}$. Thus, the alginate dissolution process of the surface-modified micro-capsule having the outer EGCG layer was different from that of the general alginate.

It was identified based on the above Example that the EGCG layer was clearly formed when the amount of EGCG used for surface-modified micro-capsule preparation was 84 mg or more per 5 ml of alginate.

Example 7. Identification of Glucose Reactivity and Insulin Secretion Ability of Islet Inside Micro-Capsule FIG. 25 shows the results of GSIS (Glucose-stimulated insulin secretion) analysis to identify the glucose reactivity and insulin secretion ability of each of the general islet, islet in alginate micro-capsule, and islet in surface-modified micro-capsule. As a result, it was identified that the islet inside the micro-capsule had lower glucose reactivity than the general islet. This is due to the slow diffusion of insulin due to the micro-capsule structure. However, there was no significant difference in terms of glucose reactivity between the islet inside the alginate micro-capsule and the islet inside the surface-modified micro-capsule. This means that the surface modification process does not affect the functionality of the islet therein.

Example 8. Evaluation of Efficacy and Efficacy Duration Via Transplantation of Surface-Modified Micro-Encapsulated Islet in Diabetic Mouse Animal Model, and Analysis of Efficacy, Duration Thereof and Morphology of Retrieved Micro-Capsules FIG. 26 shows the in-blood glucose concentration of the surface-modified micro-capsule prepared using 84 mg of EGCG dimer. To analyze the effect and shape of surface-modified micro-capsules and alginate micro-capsules, the in-blood glucose concentration and body weight of diabetic mice subjected to the islet transplantation are expressed in FIG. 27. On the 67th and 85th days after transplantation, the transplanted micro-capsules were retrieved and morphology thereof was observed with an optical microscope and is shown in FIG. 28.

First, regarding the in-blood glucose control period, the efficacy of in-blood glucose control of the surface-modified micro-capsule and alginate micro-capsule lasted for about 60 days due to statistical ineffectiveness. It was identified that a shape of the retrieved micro-capsule related to the surface-modified micro-capsule was maintained in a more stable manner than that related to the alginate micro-capsule. It was identified that in the surface-modified micro-capsule, no immune response occurred other than the cell adsorption occurred on the surface, whereas in the alginate micro-capsule, a tissue was formed therein. Taking these results together, it could be identified that surface modification of alginate micro-capsules via the EGCG treatment is an effective method to improve the structural stability of the micro-capsules.

What is claimed is:

1. A surface-modified alginate micro-capsule comprising a core-shell structure in which the core is fluidizable phase alginate, and the shell is an alginate hydrogel crosslinked with epigallocatechin gallate dimers, wherein the shell further includes an alginate coating layer, wherein the alginate coating layer has an amide bond with the epigallocatechin gallate dimer of the shell.

2. The surface-modified alginate micro-capsule of claim 1, wherein some of the epigallocatechin gallate dimers of the shell are coupled to other epigallocatechin gallate dimers via oxidation.

3. The surface-modified alginate micro-capsule of claim 1, wherein the shell comprises a plurality of hollows connected to each other in a three-dimensional manner.

4. The surface-modified alginate micro-capsule of claim 1, wherein the core is a liquid phase alginate or a mixture of liquid phase alginate and alginate hydrogel.

5. The surface-modified alginate micro-capsule of claim 1, wherein the micro-capsule provides for cell encapsulation.

* * * * *